(12) United States Patent
Spaete et al.

(10) Patent No.: US 7,592,169 B2
(45) Date of Patent: Sep. 22, 2009

(54) METHODS AND COMPOSITIONS FOR TREATMENT AND PREVENTION OF HSV-2 INFECTIONS AND CONDITIONS

(75) Inventors: Richard Roger Spaete, Emerald Hills, CA (US); George Kemble, Fremont, CA (US); Bernard Roizman, Chicago, IL (US); Mark Prichard, Birmingham, AL (US)

(73) Assignee: MedImmune, LLC, Gaithersburg, MD (US)

( * ) Notice: Subject to any disclaimer, the term of this patent is extended or adjusted under 35 U.S.C. 154(b) by 218 days.

(21) Appl. No.: 10/830,609

(22) Filed: Apr. 23, 2004

(65) Prior Publication Data
US 2005/0112142 A1 May 26, 2005

Related U.S. Application Data

(60) Provisional application No. 60/465,623, filed on Apr. 25, 2003.

(51) Int. Cl.
*C12N 7/01* (2006.01)
*C12N 7/04* (2006.01)
*C12N 15/86* (2006.01)
*C12N 15/74* (2006.01)
*C12Q 1/70* (2006.01)

(52) U.S. Cl. .................. 435/235.1; 435/5; 435/456; 435/475

(58) Field of Classification Search ........................ None
See application file for complete search history.

(56) References Cited

U.S. PATENT DOCUMENTS

| | | | |
|---|---|---|---|
| 5,328,688 A | 7/1994 | Roizman | |
| 5,922,328 A * | 7/1999 | Spector et al. | 424/231.1 |
| 6,340,673 B1 | 1/2002 | Roizman et al. | |
| 6,699,468 B1 | 3/2004 | Martuza et al. | |
| 6,846,670 B2 | 1/2005 | Schwartz et al. | |

FOREIGN PATENT DOCUMENTS

WO  WO-01-09361 A1  2/2001

OTHER PUBLICATIONS

Cassady et al., The Second-Site Mutation in the Herpes Simplex Virus Recombinants Lacking the y,34.5 Genes Precludes Shutoff of Protein Synthesis by Blocking the Phosphorylation of eIF-2a, Journal of Virology, Sep. 1998, vol. 72, No. 9, pp. 7005-7011.*
Ward et al. A novel herpes simplex virus 1 gene, UL43.5, maps antisense to the UL43 gene and encodes a protein which colocalizes in nuclear structure with capsid proteins. Journal of Virology, May 1996, vol. 70, No. 5, pp. 2684-2690.*
Boursnell, M.E. et al., "A genetically inactivated herpes simplex virus type 2 (HSV-2) vaccine . . . " J. Infect. Dis. (1997) 175:16-25.
Burke, R.L. "Current Status of HSV Vaccine Development" in The Human Herpesviruses, pp. 367-379 (1993).
Cassady, K.A. et al., "The second-site mutation in the herpes simplex virus recombinants lacking the gamma134.5 genes . . . " J. Virol. (1998) 72:7005-11.
Chou, J. et al., "Mapping of herpes simplex virus-1 neurovirulence to gamma 134.5, a gene nonessential for growth in culture" Science (1990) 250:1262-1266.
Corey, L. et al., "Recombinant glycoprotein vaccine for the prevention of genital HSV-2 infection: . . . " JAMA (1999) 282-331-40.
Inglis, S.C. "Challenges and progress in developing herpesvirus vaccines," Trends.Biotechnol. (1995) 13:135-142.
Kehm, R. et al., "In vitro expression of UL56 gene of herpes simplex virus type 1; . . . " Virus Research (1994) 33:55-66.
Koelle, D.M. and Corey, L. "Recent progress in herpes simplex virus immunobiology and vaccine research." Clin.Microbiol.Rev., (2003) 16:96-113.
McGeoch, D.J., "Comparative sequence analysis of the long repeat regions and . . . " J. Gen. Virol. (1991) 72:3057-3075.
Meignier, B. et al., "In vivo behavior of genetically engineered herpes simplex viruses R7017 and R7020: . . . " J. Infect. Dis., (1988) 158:602-614.
Meignier, B. et al., "In vivo behavior of genetically engineered herpes simplex viruses R7017 and R7020. II . . . " J. Infect. Dis. (1990) 162:313-321.
Nash, T.C. & Spivack, J.G., "The UL55 and UL56 genes of herpes simplex virus type 1 . . . " Virology (1994) 204:794-798.
Prichard, M.N. et al., "Evaluation of a recombinant live attenuated herpes simplex virus type 2 vaccine . . . " Antiviral Research (Feb. 2003) 57(3):A58.
Prichard, M.N. et al., "Evaluation of AD472, a live attenuated recombinant herpes simplex virus type 2 vaccine in guinea pigs." Vaccine, (2005) 23:5424-5431.
Rosen-Wolff, A. et al., "Determination of the coding capacity of the BamHl DNA fragment B . . . " Virus Research (1991) 20:205-221.
Spector, F.C. et al., "Evaluation of a live attenuated recombinant virus RAV 9395 as a herpes simplex virus type 2 vaccine in guinea pigs." J. Infect. Dis., (1998) 177:1143-54.
Stanberry, L.R. et al., "Prospects for control of herpes simplex virus disease through immunization." Clin.Infetc.Dis., (2000) 30:549-66.
Stanberry, L.R. et al., "Glycoprotein-D-adjuvant vaccine to prevent genital herpes." N.Engl.J.Med., (2002) 347:1652-61.
Mohr, I. et al., "A herpes simplex virus type 1 gamma34.5 second-site suppressor mutant . . . " J Virol. (2001) 75(11):5189-96.

(Continued)

*Primary Examiner*—Bruce Campell
*Assistant Examiner*—Sharon Hurt

(57) ABSTRACT

Live, attenuated, phenotypically stable HSV-2 viruses and methods of making and using the virus are provided. Live, attenuated HSV-2 viruses are constructed using recombinant techniques and can be used in a pharmaceutical composition for prophylactic treatment of HSV-2 infections and for treatment of recurrent HSV-2 related diseases and conditions.

**1

OTHER PUBLICATIONS

Ward, PL et al., "A novel herpes simplex virus 1 gene, UL43.5, maps antisense to the UL43 gene . . ." J Virol. (1996) 70(5):2684-90.

Ward, SL et al., "In vivo replication of an ICP34.5 second-site suppressor mutant following corneal infection correlates with . . ." J Virol. (2003) 77(8):4626-34.

Whitley, RJ & Roizman B. "Herpes simplex viruses: is a vaccine tenable?" J Clin Invest. (2002) 110(2):145-51.

Cassady, KA et al., "Second-site mutation outside of the U(S)10-12 domain of Deltagamma(1)34.5 herpes simplex virus 1 recombinant . . ." J Virol. (2002) 76(3):942-9.

Cassady, KA et al., "The herpes simplex virus US11 protein effectively compensates for the gamma1(34.5) gene if present before . . ." J Virol. (1998) 72(11):8620-6.

* cited by examiner

FIGURE 6

METHODS AND COMPOSITIONS FOR TREATMENT AND PREVENTION OF HSV-2 INFECTIONS AND CONDITIONS

CROSS-REFERENCE TO RELATED APPLICATIONS

This application claims the benefit under 35 U.S.C § 119(e) of U.S. Provisional Application No. 60/465,623, filed Apr. 25, 2003.

BACKGROUND OF THE INVENTION

Herpes Simplex Viruses types 1 and 2 (HSV-1 and HSV-2) are two members of the family Herpesviridae, which is defined by the architecture of the virion. B. Roizman, "Herpesviridae: A Brief Introduction" in Fields Virology, 2d ed., Vol. 2, pp. 1787-1793 (B. N. Fields and D. M. Knipe, eds. 1990). HSV-1 and HSV-2 are both members of the subfamily called the Alphaherpesvirinae, both are grouped in the E class of genome structure of the viruses comprising the family Herpesviridae, and both have a genome size of 152 kilobase pairs. HSV-1 and HSV-2 are closely related and have strong similarities in genome structure and at the nucleotide level. See McGeoch et al., J. Gen. Virol. 72:3057-3075 (1991). HSV-1 and HSV-2 are distinguishable in several aspects, including their G+C content of 67 mole % and 69 mole %, respectively. Also, the sequences in the HSV-1 and HSV-2 $R_L$ regions are more divergent than in the $U_L$ and $U_S$ regions. McGeoch et al., J. Gen. Virol. 72:3057-3075 (1991). HSV-1 and HSV-2 also differ in restriction enzyme cleavage sites and in the sizes of viral proteins. Roizman & Sears, "Herpes Simplex Viruses and Their Replication" in Fields Virology, 2d ed., Vol. 2, pp. 1795-1817 (B. N. Fields and D. M. Knipe, eds. 1990).

HSV-1 infections are extremely common and affect from 70-80 percent of the total population in the United States. HSV-1 is transmitted via oral secretions, respiratory droplets or direct oral contact, and results in lesions or blisters on the mouth and lips. HSV-2 is transmitted venereally and causes ulcers and lesions on the genitals and surrounding areas, which can result in urinary retention, neuralgia and meningoencephalitis. Both HSV-1 and HSV-2 can cause either oropharyngeal or genital lesions that are indistinguishable.

There are many HSV-2 viral strains currently known, including HSV-2 strains G, HG52, and 333. The nucleotide sequences encompassing UL55, UL56 and a proposed ICP34.5 of HSV-2 strain HG52 have been sequenced. McGeoch et al., J. Gen. Virol. (1991). A restriction map for the HSV-2 strain HG52 has also been published in Chartrand, et al., J. Gen. Virol. 52:121-133 (1981), which is incorporated herein by reference. The HSV-2 strains G and 333 have the same BamHI, BspEI, EcoRI and Hind III restriction maps in the locale of the tk gene. The HSV-2 HG52 and G strains also have the same NcoI and BsgI restriction maps in the locale of the UL55 and UL56 genes. In the locale of the proposed HSV-2 ICP34.5 gene, HSV-2 strains HG52 and G have very similar EcoO109I and SphI restriction sites. The HSV-2 virus includes all viral strains that have been classified as HSV-2 by the Herpesvirus Study Group of the International Committee on the Taxonomy of Viruses (ICTV). See e.g., Roizman B et al., Herpesviridae, Definition, provisional nomenclature and taxonomy in Intervirology 16:201-217 (1981).

HSV-2, like other herpesviruses, has the ability to establish both a primary and a latent infection in its host. During the primary infection, HSV-2 infects the skin and epithelial cells and then spreads to the ganglia of the peripheral nervous system. After the lesions from the primary infection have healed, the HSV-2 viral DNA can remain dormant in the ganglia. This dormant or inert state is referred to as a state of latency. Periodically, the HSV-2 can become reactivated and cause lesions around the initial site of infection. During the recurrent disease episodes, the infectious HSV-2 virus particles are shed from the lesions. From a clinical perspective, this recurrence of HSV-2 infection is particularly problematic because it can occur up to ten times per year, can cause severe physical and psychological discomfort and creates the risk of infecting the patient's sexual partners. In certain individuals, recurrent infections may be asymptomatic, which can lead to inadvertent HSV-2 infection of others.

The number of individuals infected with HSV-2 in the United States is estimated to range from 40 to 60 million, and from 0.5 to 1 million new cases of genital herpes are diagnosed annually in the United States. See R. Whitley and J. Gnann, "The Epidemiology and Clinical Manifestations of Herpes Simplex Virus Infections" in The Human Herpesviruses, pp. 69-105 (Roizman, B., R. J. Whitley and C. Lopez eds., 1993). HSV-2 infection worldwide continues to increase.

Two groups that suffer the most severe forms of herpetic diseases caused by HSV-2 are infants or immunocompromised individuals. HSV-2 infection of neonates can result in encephalitis, skin lesions, keratoconjunctivitis, widely disseminated infections, microcephaly or hydranencephaly. Neonatal HSV-2 infection is almost always symptomatic and frequently lethal. Herpes simplex virus infections of the genital tract are also of special concern because of the possibility that genital ulceration may facilitate the transmission of human immunodeficiency virus (HIV) Holmberg et al., JAMA, 19,259:1048-50 (1988).

Currently, the major therapeutic treatment for recurrent HSV-2 infections is administration of acyclovir, which reduces the duration and severity of primary infection as well as the frequency of recurrence, but does not prevent asymptomatic viral shedding or the establishment of latency. The high incidence of HSV-2 infection, recurrent disease episodes, and asymptomatic transmission suggest that the best treatment will be a prophylactic treatment capable of preventing or ameliorating HSV-2-related diseases or conditions.

A number of different approaches to the development of HSV vaccines have been attempted, including live, attenuated HSV viruses, live virus vectors, killed virus vaccines and subunit protein vaccines. See R. L. Burke, "Current Status of HSV Vaccine Development" in The Human Herpesviruses, pp. 367-379 (B. Roizman, R. J. Whitley, and C. Lopez eds., 1993). A live virus vaccine is distinguishable from a killed virus vaccine in that the live virus is able to replicate, whereas the killed virus preparations are inactivated with, e.g., phenol, formaldehyde, heat or ultraviolet light, and are unable to replicate. Thus, the term "live" when used to describe a virus means that it is capable of replication. An attenuated virus is one that does not cause physical signs of disease and reduces person-to-person dissemination. An attenuated virus may still be capable of establishing latency. The advantage of a live, attenuated HSV-2 virus vaccine is that the live, attenuated HSV-2 virus can present a range of viral antigens to the host and stimulate both cell-mediated and humoral immune responses, which are both important in protection against HSV-2-related diseases and conditions. See S. C. Inglis, "Challenges and progress in developing herpesvirus vaccines," Tibtech vol. 13, pp. 135-142 (April 1995). Attempts at producing an effective HSV-2 subunit vaccine have Two of the most comprehensively developed live, attenuated HSV vaccines are recombinant derivatives of HSV-1 strain F, called R7017 and R7020. Meignier et al., *J. Infect. Dis.*, 158:602-614 (1990). R7020 consists of the HSV-1 strain F genome having selected deletions and insertions. Results of human vaccine trials with R7020 indicate that while it is extremely safe, it is over attenuated for purposes of eliciting immunological protection against HSV-2 in humans. Thus, there remains a need in the art for a live, attenuated viral composition for the prophylactic treatment of HSV-2.

Little is known about the functions of the UL55 and UL56 gene products, except that they appear to be nonessential genes and do not share any sequence homology suggesting functional similarity. Nash & Spivack, *Virology* 204:794-798 (1994). The sequence of the UL55 and UL56 genes of HSV-2 strain HG52 has been described by McGeoch, *J. Gen. Virol.* 72:3057-3075 (1991) and is incorporated herein by reference. The UL56 gene of HSV-1 strain F has been cloned and expressed to produce recombinant polypeptides that are immunoreactive with antibodies in human HSV-1 IgM-positive sera. See, Kehm et al., Virus Research 33:55-56 (1994).

The HSV genome contains two copies of the $\gamma_1 34.5$ nucleotide sequence that encodes the Infected Cell Protein 34.5 ("ICP34.5"). There is one $\gamma_1 34.5$ nucleotide sequence in each of the inverted repeats flanking the long unique sequence of HSV-1. Chou et al., *Science* 250:1262-1266 (1990). A proposed sequence of ICP34.5 in HSV-2 strain HG52 has been disclosed. McGeogh, *J. of Gen. Vir.* 72:3057-3075 (1991), which is herein incorporated by reference. The ICP34.5 nucleotide sequence is predicted to encode a protein of 261 amino acids. In contrast, the HSV-1 ICP34.5 sequence is predicted to encode a protein of 263 amino acids. Although the $\gamma_1 34.5$ open reading frame is conserved among the HSVs, the $\gamma_1 34.5$ open reading frame is not highly conserved among other members of the herpesvirus family.

Protein Kinase R (PKR) is an important component of host responses to infection (e.g., viral infection). The enzyme is inactive in uninfected unstressed cells, but can be induced by double-stranded RNA and interferon. Upon activation, PKR phosphorylates key proteins, among which is the α subunit of eukaryotic elongation factor 2 (eIF-2α). Activation of PKR is a common mechanism by which eukaryotic cells respond to the presence of and gene expression by infectious agents. The PKR cascade curtails viral replication and thereby spares the organism in the interim between infection and immune response. See, e.g., Cassady et al. (*J. Virol*, 76:942-949 (2002).

It has previously been reported that, in HSV-1, the $\gamma_1 34.5$ gene product inhibits the phosphorylation of eIF-2α, thereby enabling uninterrupted viral protein synthesis. It has also been reported that the $U_s 11$ gene product of HSV-1 can block the shutoff of protein synthesis by inhibiting phosphorylation of eIF-2α. See, Cassady et al. (*J. of Vir.*, 72:8620-8626 (1998)), which is incorporated by reference herein. While the mechanism by which the $U_s 11$ gene product acts on eIF-2α phosphorylation is unknown, there is evidence that $U_s 11$ can compensate for certain $\gamma_1 34.5$ knockouts in HSV-1. See, Id.

Little is known about the $U_L$ 43.5 gene product other than it appears to be in accessory protein associated with structures involved in HSV-1 capsid assembly. See, e.g., Ward et al., *J. of Vir.*, 70:2684-2690 (1996)).

BRIEF SUMMARY OF THE INVENTION

It is an object of the invention to provide live, attenuated HSV-2 viruses. It is also an object of the invention to provide live, attenuated HSV-2 viruses for the purposes of using the virus as an immunogenic composition for the prevention or amerlioration of HSV-2 and/or HSV-1 infection. The live, attenuated HSV-2 viruses of the invention can also be referred to as recombinant HSV-2 viruses or as HSV-2 deletion viruses or HSV-2 mutants. AD472 described herein is a preferred embodiment of the attenuated HSV-2 viruses encompassed by the present invention.

One preferred embodiment of the invention is a live, attenuated HSV-2 virus characterized by having both copies of the ICP34.5 nucleotide sequence deleted; the UL56 nucleotide sequence deleted; a portion or all of the UL55 nucleotide sequence deleted; a mutation or deletion of the $U_s 10$-$U_s 12$ nucleotide sequence (preferably $U_s 11$, more preferably $U_s 11$ and Us12); and a mutation or deletion of the $U_L 43.5$ nucleotide sequence.

In another nonexclusive embodiment, a live attenuated virus is provided having any combination of the above genes deleted (all or part of the genes) or mutated.

Preferably, the portion of UL55 that is deleted from the live, attenuated HSV-2 virus of the invention is that sequence extending from the BsgI site located 102 base pairs from the UL55 start codon to the end of the UL55 coding sequence. The invention includes any HSV-2 strain that has at least a single base pair deletion or mutation in all of the following: both copies of the ICP34.5 nucleotide sequence, the UL55 nucleotide sequence and the UL56 nucleotide sequence, preferably the deletions are at least 100 bases long and in the coding region, and a mutation or deletion of the $U_s 10$-$U_s 12$ genes, most preferably the $U_s 11$ coding region; and a mutation or deletion of the $U_L 43.5$ gene.

The mutations in each of the ICP34.5, UL55, UL56, $U_s 10$-$U_s 12$ (preferably $U_s 11$, more preferably $U_s 11$ and $U_s 12$), and $U_L 43.5$ nucleotide sequences usually have the effect of altering the amino acid composition of the resulting polypeptides or disrupting the expression of the full polypeptide or completely inactivating expression of these polypeptides.

A recombinant HSV-2 virus of the invention comprises mutations of the ICP34.5, UL55, UL56, $U_s 10$-$U_s 12$ (preferably $U_s 11$, more preferably $U_s 11$ and Us12), and $U_L 43.5$ genes (and any combination thereof), that are modified by insertion, deletion, nucleic acid substitution or deletion, or by insertion of a codon that stops translation of the gene, in order to detrimentally affect virulence while retaining the immunogenic character of HSV-2.

These live attenuated HSV-2 viruses offer several advantages over the known live, attenuated HSV viruses developed for prophylactic treatment of HSV: (1) the deletions were selectively chosen to avoid over attenuation of the HSV-2 virus such that the resulting virus would be efficacious for prophylactic treatment of HSV infections and conditions as well as safe; (2) the deletion of the coding sequence for the ICP34.5 and $U_s 11$ proteins were selected to ensure replication incompetence in the central nervous system; (3) the use of HSV-2 rather than HSV-1 as the parent virus ensured an appropriate cytotoxic T lymphocyte response to infection by HSV-2; and (4) the attenuated viruses (e.g., AD472) are genetically and phenotypically stable.

The parent virus from which the live, attenuated viruses of the invention are derived can be any HSV-2 strain. Many strains of HSV-2 have been isolated. Few HSV-2 strains have been sequenced, but many have been analyzed for restriction fragment length polymorphisms. These strains are largely conserved at the nucleotide level.

As another aspect of the invention, a method is provided for making a live, attenuated HSV-2 virus comprising providing an isolated HSV-2 virus; mutating a portion of each of the two copies of the $\gamma_1 34.5$ nucleotide sequence; mutating a portion of the UL56 nucleotide sequence; mutating a portion of the UL55 nucleotide sequence; mutating a portion of the $U_s10$-$U_s12$ (preferably $U_s11$, more preferably $U_s11$ and Us12) nucleotide sequence; mutating a portion of the $U_L43.5$ nucleotide sequence (or any combination of the gene nucleotide sequences). The portions of the $\gamma_1 34.5$, UL55, UL56, $U_s10$-$U_s12$ (preferably $U_s11$, more preferably $U_s11$ and Us12), and the $U_L43.5$ nucleotide sequences that are to be mutated range from any single base pair to the full nucleotide sequences, including any intermediate-size deletions or mutations that result in attenuation of the HSV-2 virus. The mutations to be introduced usually have the effect of altering any polypeptides expressed from the $\gamma_1 34.5$, UL55, UL56, $U_s10$-$U_s12$ (preferably $U_s11$, more preferably $U_s11$ and $U_s12$), and the $U_L43.5$ nucleotide sequences, compared to the corresponding polypeptides expressed from the parent HSV-2 strain.

Another preferred embodiment of the invention is a method of preventing HSV-2 infection, disease, or recurrence of disease comprising administering to an individual vaccine compositions comprising an attenuated HSV-2 virus of the invention.

Another preferred embodiment of the invention is a method for making an attenuated, genetically stable HSV virus comprising introducing a mutation or deletion into a $\gamma_1 34.5$ gene (one or both copies) and $U_s$ 11 gene of a HSV viral genome.

The portion of the UL55 nucleotide sequence to be mutated preferably comprises a deletion of at least the nucleotide sequence from the BsgI site located 102 base pairs from the start codon to the end of the UL55 nucleotide sequence in any HSV-2 strain having the same BsgI restriction site at position 102 as that of the HSV-2 HG52 strain, including HSV-2(G) and HSV-2 strain 333.

As yet another aspect of the invention, an isolated polypeptide is provided, comprising a fusion protein having at least an immunogenic portion of an HSV-2 UL56 polypeptide fused to a Glutathione S Transferase (GST) polypeptide, wherein the GST polypeptide is at the amino terminus of the fusion protein and the HSV-2 UL56 polypeptide portion is at the carboxyl terminus of the fusion protein. The GST-UL56 fusion polypeptide that contains the entire UL56 polypeptide fused to a full GST polypeptide is approximately 52 kilodaltons. However, the GST-UL56 fusion proteins of the invention can contain smaller portions of the UL56 polypeptide that are immunogenic and therefore can be expected to be smaller than 52 kD.

These GST-UL56 fusion proteins are useful for many purposes, including confirming whether recombinant HSV-2 viruses express UL56, developing polyclonal antisera or monoclonal antibodies specific to epitopes of the HSV-2 UL56 protein; and developing an immunoassay to detect the expression of HSV-2 UL56 in a sample. The GST-UL56 fusion proteins of the invention can also be used as a type-specific reagent capable of discerning HSV-1 from HSV-2.

As a further aspect of the invention, a plasmid is described that expresses a fusion protein comprising at least an immunogenic portion of the HSV-2 UL56 polypeptide and the Glutathione S Transferase (GST) polypeptide. The plasmid of the invention comprises an HSV-2 UL56 nucleotide sequence comprising at least a sequence encoding an immunogenic portion of the HSV-2 UL56 polypeptide up to and including the entire 708 base pair HSV-2 UL56 nucleotide sequence. This UL56 nucleotide sequence is inserted into the pGEX5.3 GST fusion protein vector such that the UL56 open reading frame is in frame with the GST open reading frame. The plasmid of the invention also includes a plasmid comprising the entire 708 base pair HSV-2 UL56 open reading frame from the ATG to the stop codon, said entire HSV-2 UL56 reading frame inserted into the pGEX5.3 GST fusion vector, wherein the UL56 open reading frame is in frame with the GST open reading frame. The invention includes a composition comprising a polyclonal antisera generated by immunizing a mammal with an isolated GST-UL56 fusion protein. The polyclonal antisera is useful for assaying for the presence of HSV-2 UL56 in a sample and confirming expression of HSV-2 UL56 in an expression system.

GST versions of ICP34.5, UL55, $U_s10$, $U_s11$, $U_s12$ and the $U_L43.5$ polypeptide sequences are also contemplated.

As yet a further aspect, the live, attenuated HSV-2 virus of the present invention may be used in therapeutic and/or immunogenic compositions for preventing and treating HSV-related conditions and diseases. The pharmaceutical compositions of the invention can be used for the prophylactic treatment of an HSV-1 or HSV-2 related disease or condition and comprises an immunizingly effective amount of a live, attenuated HSV-2 virus of the invention in a suitable pharmaceutical vehicle. This pharmaceutical composition can be used to generate a neutralizing immune response to HSV-2 infection, for prophylactic treatment of HSV-1 or HSV-2 infection and amelioration of HSV-1 or HSV-2 related conditions, and for prevention of recurrent HSV-1 or HSV-2 disease symptoms. A human host can be inoculated intramuscularly or subcutaneously with a pharmaceutical composition of the invention comprising an immunity-inducing dose of one or more of the recombinant HSV-2 viruses described herein. Other modes of inoculation include surface scarification or inoculation of a body cavity. Generally, effective immunization of a human host can be achieved by one to several inoculations of between 10 and 1,000,000 pfu each, as measured in susceptible human or nonhuman primate cell lines, preferably 1,000 to 1,000,000 pfu will be used.

The following are exemplary indications for vaccination: (1) a need to boost the host's level of immunity; (2) a lack of immunity combined with a high probability of natural infection; and (3) a lack of immunity and a high likelihood that the subject will become immunocompromised due to immunosuppressive therapy in the near future. The pharmaceutical composition according to the present invention can be used in liquid form or in freeze-dried form with suitable preservatives and protective agents to preserve the viral strains during the freeze drying process.

As still another aspect, a method is described for the prophylactic treatment of a herpes simplex type 2-related disease or condition in a mammal comprising administering an immunizingly effective amount of a pharmaceutical composition to a mammal. The pharmaceutical composition comprises a live, attenuated HSV-2 virus having at least a single base pair deletion or mutation in all or some of the following: both copies of the ICP34.5 nucleotide sequence, the UL55 nucleotide sequence, the UL56 nucleotide sequence and $U_s10$-$U_s12$ (preferably $U_s11$, more preferably $U_s11$ and Us12) nucleotide sequence, and the $U_L43.5$ nucleotide sequences. The deletions or mutations in each of the ICP34.5, UL55, UL56 and $U_s10$-$U_s12$ (preferably $U_s11$, more preferably $U_s11$ and Us12), and $U_L43.5$ nucleotide sequences usually have the effect of altering the amino acid composition of the resulting polypeptides or disrupting the expression of the full polypeptides or completely inactivating expression of these polypeptides. Preferably, the method of prophylactic treatment is designed for human patients with HSV-1 or HSV-2-related diseases or conditions.

Another embodiment of invention is a method for using the attenuated HSV-2 viruses of the invention as a vaccine vector for delivering an effective amount of antigen to an animal, preferably a human.

Another alternative embodiment of the invention is the use of attenuated HSV viruses of the invention for treating malignancy disorders (i.e., as an oncolytic HSV virus). Representative uses of oncolytic HSV viruses and methods of constructing oncolytic viruses are described, for example, in Nakamori et al., *Clin Cancer Res.* 2003 July;9(7):2727-33, Lou, E., Ann Med. 2004;36(1):2-8.; Lou, E., *Acta Oncol.* 2003;42(7):660-71; Shah et al., *J Neurooncol.* 2003 December;65(3):203-26; Thomas et. Al. Mol Ther. 2003 October;8 (4):543-51, and U.S. Pat. Nos. 6,172,047, 6,340,673, and 6,699,468. It is also specifically contemplated that known oncolytic HSV viruses could be made more genetically and/or phenotypically stable by deleting or mutating the Us11, and/or the $U_s10$ and/or the Us12 polynucleotides.

BRIEF DESCRIPTION OF THE DRAWINGS

FIG. 6 is a diagram depicting the genetic stability of AD472.

DETAILED DESCRIPTION OF THE INVENTION

Figure 1:
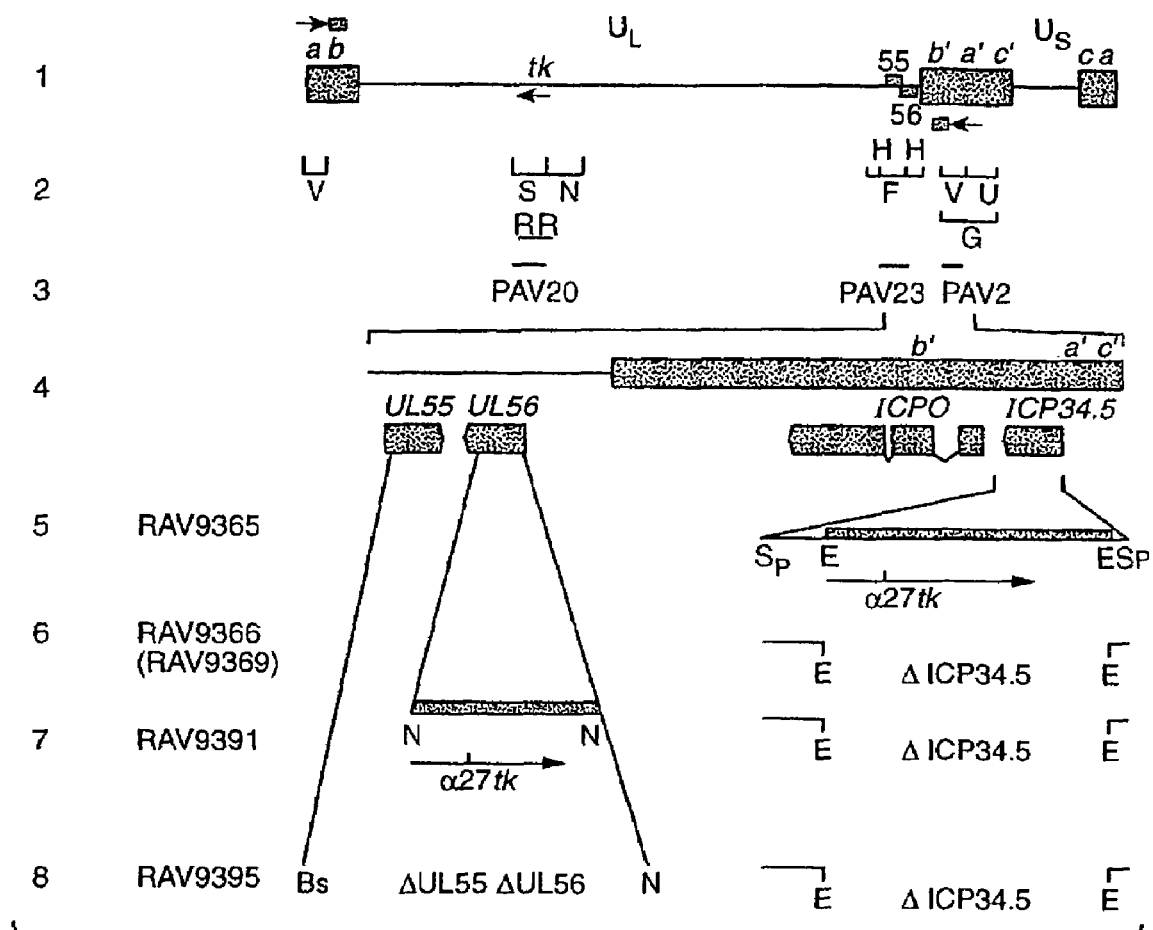
FIG. 1 is a schematic diagram showing the genetic organization of RAV 9395 and the other recombinant HSV-2 viruses that were constructed in the process of constructing RAV 9395.

The present invention provides a method of constructing recombinant HSV-2 viruses that are live, attenuated HSV-2 for use as a prophylactic treatment for HSV-1 or HSV-2 infections and HSV-1 or HSV-2-related diseases and conditions.

For example, in order to construct a desired recombinant HSV-2 virus, RAV 9395, viral DNA of intermediate recombinant HSV-2 viruses was purified from viral lysates using standard procedures and analyzed by Southern blot, using DNA probes that were labeled with $^{32}$P using a nick translation kit. In order to confirm whether the recombinant HSV-2 viruses expressed UL56, the 708 bp HSV-2 UL56 open reading frame was cloned from HSV-2 strain G into a fusion protein vector. The UL56 open reading frame was cloned in frame with the Glutathione-S-transferase fusion protein, and the resulting plasmid, PAV116, was used to transform a bacterial culture. The induction of the GST-UL56 fusion protein was confirmed by SDS polyacrylamide gel electrophoresis followed by coomassie blue staining. The fusion protein was purified by affinity chromatography, and the purified preparation was used to immunize rabbits for production of polyclonal antiserum specific to HSV-2 UL56. After additional booster immunizations with the affinity purified GST-UL56 fusion protein, the presence of UL56-specific antibodies in the rabbit sera was tested using Western blots of HSV-2(G) infected cell lysates probed with the rabbit polyclonal antisera raised against the GSTUL56 fusion protein.

In order to assay the recombinant HSV-2 viruses for expression of UL56, the viruses were grown on cell monolayers that were harvested and lysed. The proteins were separated in denaturing polyacrylamide gels and transferred to nitrocellulose using well-known procedures. After blocking treatment, the nitrocellulose blots containing proteins expressed by the cells infected by the recombinant HSV-2 viruses, were incubated with the rabbit polyclonal antiserum raised against the GST-UL56 fusion protein. Bound rabbit antibodies were detected by using goat anti-rabbit IgG conjugated to alkaline phosphatase and substrates Nitro blue tetrazolium and 5-bromo-4-chloro-3-indolyl for a colorimetric reaction.

The recombinant HSV-2 virus RAV 9395 was constructed through a series of insertions and deletions to the HSV-2 strain G. RAV 9395 has the entire UL56 nucleotide sequence, both copies of the ICP34.5 nucleotide sequence, and a portion of the UL55 nucleotide sequence deleted. In order to construct the recombinant HSV-2 virus, RAV 9395, the parent strain, HSV-2 (G) was used. A series of insertions and deletions using selection for thymidine kinase was conducted according to the procedure described by Post and Roizman, *Cell* 25:227-232 (1981). This procedure allows the introduction of site-specific mutations or deletions that are introduced by co-transfection with a deletion or insertion plasmid that contains flanking nucleotide sequences that recombine with the co-transfected parent viral strain to be altered.

The live, attenuated HSV-2 vaccine candidate, designated RAV 9395, had the following nucleotide sequences deleted from the HSV-2(G) parent strain: (1) a 1033 bp deletion in each of the two $\gamma_1$34.5 nucleotide sequences, the deletions stretching from the EcoO109I site located 16 bp from the start codon of the ICP34.5 open reading frame to the EcoO109I site located 110 bp after the stop codon of the ICP34.5 open reading frame; and (2) a deletion from the NcoI site at the start codon of the UL56 gene to the BsgI site located 102 bp from the start codon of the UL55 open reading frame. These deletions comprised a 923 bp deletion in both copies of the ICP34.5 nucleotide sequence and all of the UL56 nucleotide sequence and approximately the last 458 bp of the UL55 gene. RAV 9395 contains an intact, functional tk gene.

Figure 5:
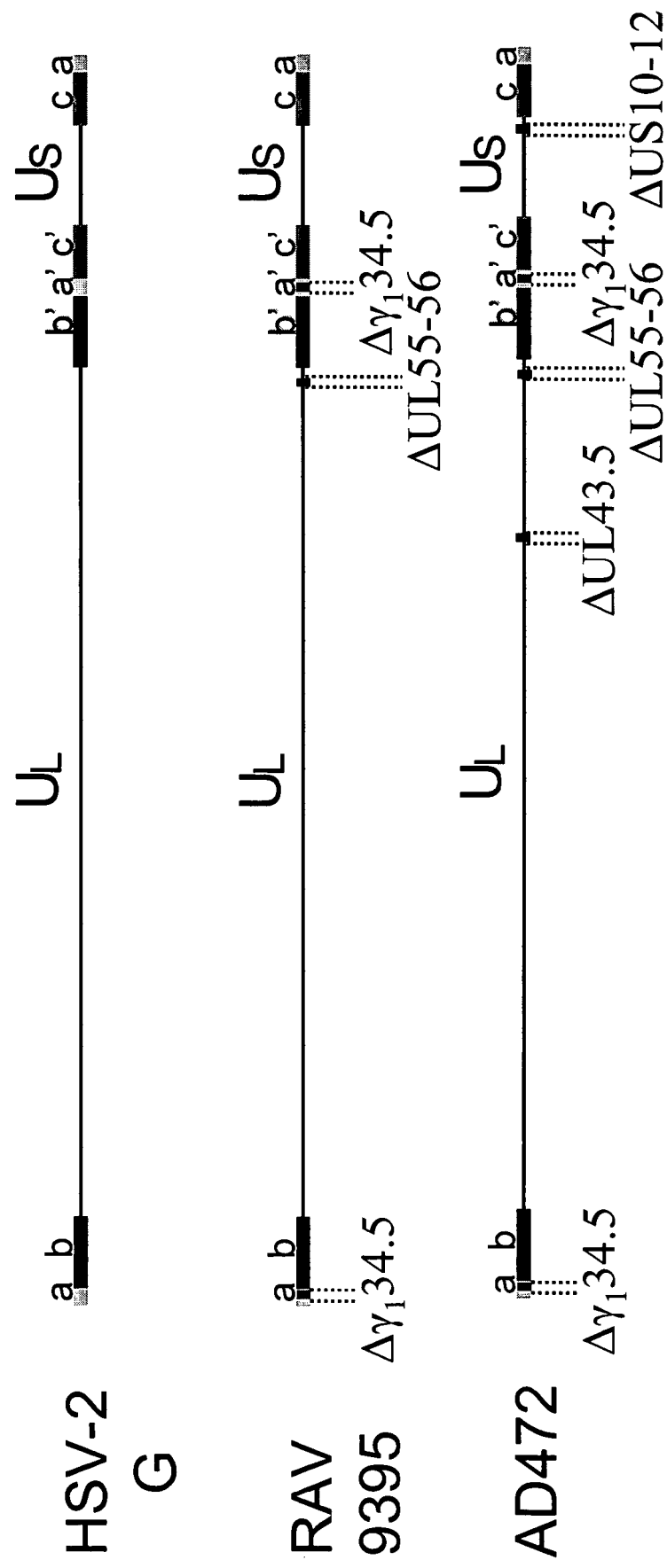
FIG. 5 is a diagram depicting the genes which have been deleted resulting in two attenuated viruses of the invention, RAV9395 and AD472.

AD472 was constructed from a set of six overlapping cosmid clones. These clones were derived from RAV 9394, the tk$^-$ predecessor of RAV 9395, and were used to reproduce the same ICP34.5 and UL55-56 deletions as described in RAV 9395 [Spector et al., 1998, *J Infect Dis*, 177(5):1143-54, which is herein incorporated by reference]. Cosmid clone scpt43.5 was used to delete UL43.5 via a 7.3 kb deletion and cosmid AD467 was used to delete the $U_S10$-12 region in the final virus. Thus, the genotype for AD472 is $\Delta\gamma_1 34.5$, $\Delta UL55$, $\Delta UL56$, $\Delta UL43.5$, and $\Delta U_S10$-12 (see FIG. 5). AD472 was deposited with the American Type Culture Collection ("ATCC") 10801 University Boulevard, Manassas, Va. 20110-2209 on Jun. 6, 2008, ATTCC Patent Deposit Designation: PTA-9242.

Using the methods described herein or otherwise known in the art, other recombinant HSV-2 viruses can be constructed having a range of mutations or deletions in one or both copies of the $\gamma_1 34.5$ nucleotide sequence, the UL55 nucleotide sequence, the UL56 nucleotide sequence, the $U_s10$-$U_s12$ (preferably $U_s11$, more preferably $U_s11$ and Us12) nucleotide sequence, and $U_L43.5$ nucleotide sequence (or any combination thereof).

The RAV 9395 recombinant HSV-2 virus was used to immunize intramuscularly *Aotus trivirgatus* sp. monkeys with varying doses, ranging from $10^3$, $10^4$, $10^5$, and $10^6$ plaque forming units (pfu). The *Aotus* monkey is exquisitely sensitive to HSV-infection and is therefore an animal model that closely approximates the neonate. Thirty days after immunization, the monkeys were challenged with $10^2$ pfu of wild type HSV-2 (G), which is normally a lethal dose. All animals survived the challenge, and all three animals immunized with the $10^3$, $10^4$, and $10^5$ pfu doses of RAV 9395 showed no disease symptoms and only some weight loss. The animal receiving the $10^6$ pfu dosage of RAV 9395 exhibited some discharge at the injection site, some weight loss, and some isolated lesions at distant sites. The animal tolerated these lesions well and later recovered completely. Because the *Aotus* monkey is exquisitely sensitive to HSV infection, these results show that RAV 9395 is a promising candidate for a safe and effective prophylactic treatment of HSV-2 infection in humans. Based upon well-known techniques for calculating dosages and immunization protocols, the RAV 9395 as well as the range of recombinant HSV-2 viruses described herein can be used in a pharmaceutical composition for both the prophylactic treatment of HSV-2 infection as well as treatment for recurrent HSV-2 disease symptoms and conditions.

Figure 6:
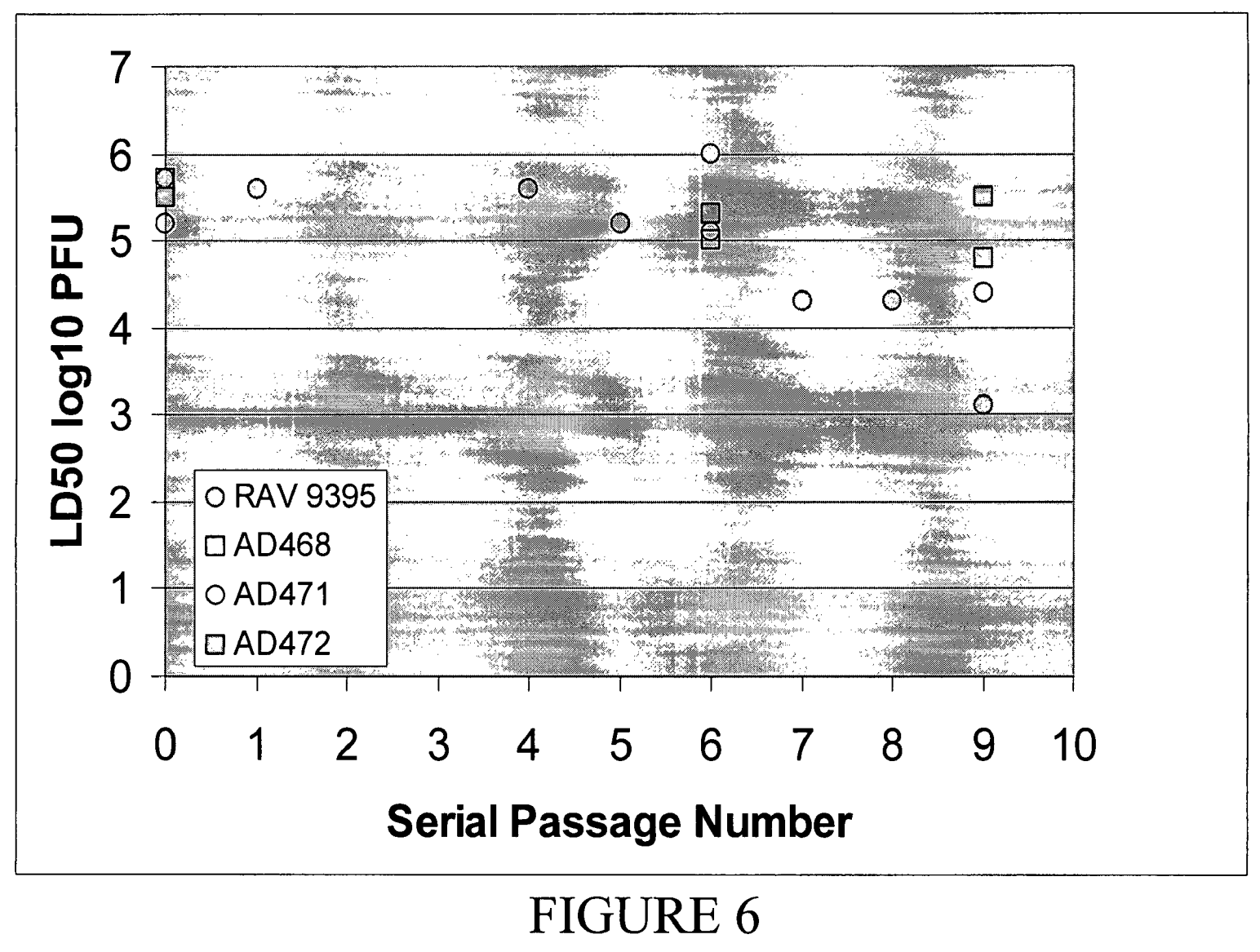

The present invention provides attenuated HSV-2 viruses with increased genetic and phenotypic stability over previously known HSV-2 viruses, including RAV9395. In a preferred embodiment, the $U_s11$ region of the viral genome is deleted to improve genetic and phenotypic stability. An exemplary virus is referred to as AD472 herein. Three separate AD472 isolates were passaged nine times through the CNS of mice and $LD_{50}$ values were ascertained following passage 1, 6, and 9 (FIG. 6). Each of the independent isolates remained highly attenuated in the CNS even after 9 serial passages in this system suggesting that this set of mutations conferred both attenuation as well as genetic and phenotypic stability of the vaccine virus.

A live, attenuated HSV-2 virus and the methods and products of the present invention are further described in the following examples, which are intended to illustrate the invention without limiting its scope.

EXAMPLES

Example 1

Materials and Methods

Cells and Viruses.

$tk^+$ and $tk^-$ viruses were selected in human 143TK− cells. Hep-2, Vero, MRC-5, 10T1/2 and SK-N-SH neuroblastoma cell lines were used for protein analyses and growth characteristics of the recombinant viruses constructed in this study. All cell lines except MRC-5 and 10T1/2 were maintained in minimum essential medium (MEM) (JRH Biosciences, Lenexa, Kans.) supplemented with 10% fetal calf serum (FCS) (JRH Biosciences, Lenexa, Kans.), L-glutamine (2 mM), penicillin (100 units/ml), streptomycin (0.1 mg/ml) and pyruvate (1 mM). MRC-5 cells were maintained in Dulbecco's modified Eagle's medium (DME) (JRH Biosciences, Lenexa, Kans.) plus 10% FCS and supplemented as above. 10T1/2 cells were maintained in basal Eagle's medium (BME) (Sigma, St. Louis, Mo.) plus 10% FCS and supplemented as above. Prior to experimentation all cells were transferred to DME plus 10% FCS. For selection of $tk^+$ viruses, this medium was supplemented with $1.1 \times 10^4$ M hypoxanthine, $4.5 \times 10^{-7}$ M aminopterin and $2 \times 10^{-5}$ M thymidine (HAT) (Sigma, St Louis, Mo.) and for $tk^{31}$ virus selection, the medium was supplemented with 40 mg/ml of bromodeoxyuridine (BUdR) (Sigma, St Louis, Mo.). Infections were performed in a volume of 1 ml on T25 dishes. The virus inoculum was allowed to adsorb for 1 hour at 37 degrees C., removed and the infected cell monolayers were overlayed DME containing 1% FCS and incubated at 37 degrees C. To pick plaques, the overlay media was supplemented with human immune globulin (Miles, Elkart, Ind.) at 0.1 ml/100 ml medium. The recombinants were routinely plaque purified twice under selection on 143 cells and twice on Vero cells.

Reagents and Plasmids.

Restriction enzymes were obtained from New England BioLabs, Beverly, Mass. T4 DNA polymerase and ligase were obtained from Boehringer Mannheim Biochemicals, Indianapolis, Ind. Oligonucleotides were produced in-house and were synthesized on an ABI 392 instrument (Applied Biosystems, Foster City, Calif.).

Purification and Analyses of Viral DNA.

Viral DNA intended for transfections was prepared from NaI (J. T. Baker Inc, Phillipsburg, N.J.) gradients according to the method of Walboomers and Ter Schagget 1976. (A new method for the isolation of herpes simplex virus 2 DNA. Virology 74: 256-258.) Briefly, three roller bottles of Vero cells were infected at approximately 1 plaque forming unit (pfu)/cell with the appropriate recombinant virus. The virus was then propagated at 34° C. for 48 hours till the cytopathic effect (CPE) was 100%. The infected cells were then shaken into the media and the cells were centrifuged at low speed to pellet the infected cells. The infected cells were then resuspended in PBS (JRH Biosciences, Lenexa, Kans.) and the nuclei were solubilized by the addition of 0.6% Nonidet P40 (NP40) (Sigma). The cells were incubated on ice for 15 minutes with occasional vortexing. The nuclei were then removed by centrifugation at 1500 rpm in a Beckman bench centrifuge. The supernatant containing the viral DNA was removed and EDTA (Sigma), proteinase K (Boehringer Mannheim), and sodium dodecyl sulfate (SDS) (Sigma) were added to final concentrations of 25 mM, 100 mg/ml and 0.5% respectively.

The DNA solution was incubated for at least 1 hour at 37° C. before being loaded on to a 40 ml gradient of saturated NaI containing 6 mg/ml Ethidium Bromide. The gradients were centrifuged at 45,000 rpm overnight in a Beckman VTi50 rotor. The DNA was harvested from the gradient and the ethidium was removed by 3 extractions with isoamyl alcohol. The DNA solution was extensively dialysed against at least 4 changes of 0.01 M Tris and 0.01 M EDTA (TE). The first dialysis solution also contained 100 mM NaCl to facilitate the removal of iodine from the DNA. For small scale preparations, viral DNA was purified by phenol-chloroform extraction of cytoplasmic fractions of infected Vero cells. The viral DNA was analyzed by the method of Southern. Viral DNA was digested with restriction enzymes according to the manufacturer's specifications and the DNA fragments were electrophoretically separated on 0.8% agarose gels containing Tris phosphate buffer (1×TPE) by standard techniques (Maniatis et al., 1982). The separated fragments were then transferred to Hybond-N+ nylon membranes (Amersham Corp.), in the presence of 20×SSC (3 M NaCl, 0.3 M sodium citrate) and immobilized using a UV Crosslinker 1000 (Hoefer Scientific Instruments, San Francisco, Calif.). The membrane with the immobilized DNA fragments was then hybridized to $^{32}P$ radiolabeled, denatured DNA probes overnight at 65° C. in a mixture of 0.6 M NaCl, 50 mM sodium citrate (pH7.0), 0.1% SDS, 100 mg/ml of denatured salmon sperm DNA (Boehringer Mannheim), 0.02% Ficoll (type 400-DL; Sigma), 0.02% polyvinylpyrolidone and 0.02% bovine serum albumin (fraction V). The blot was washed four times in an excess volume of a solution containing 60 mM NaCl, 20 mM sodium citrate (pH 7.0), and 0.1% SDS for 15 minutes at 65° C. The DNA probes were radiolabeled with $\alpha^{32}P$ dCTP by nick translation according to manufacturer specifications of a kit designed for this purpose (Du Pont, Wilmington, Del.).

Expression of UL56 as a GST Fusion Protein.

Figure 4:
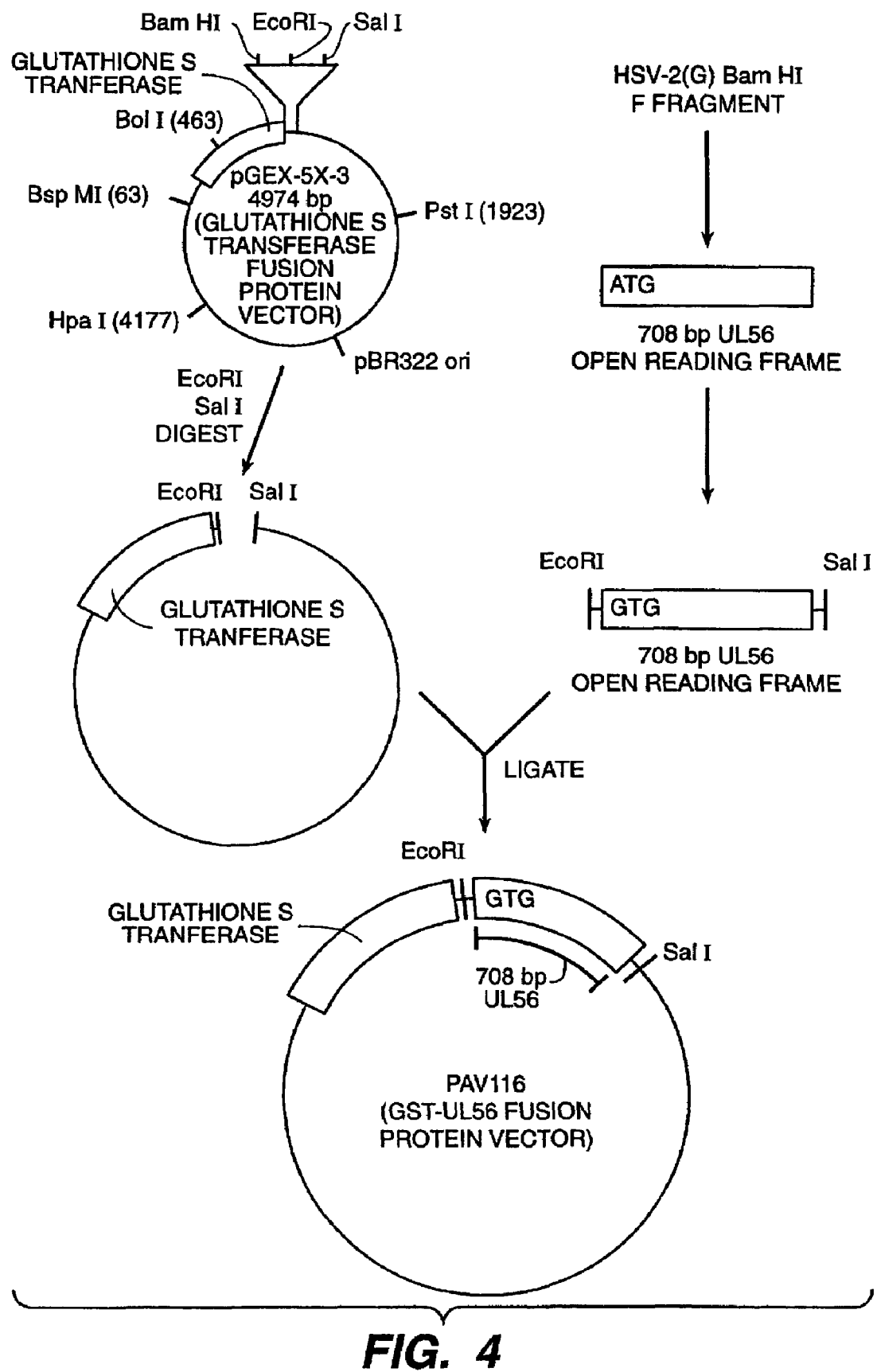
FIG. 4 is a diagram depicting the construction of the GST-UL56 fusion protein vector, PAV116.

The entire 708 base pair (bp) UL56 open reading frame from the ATG to the stop codon was amplified by polymerase chain reaction (PCR) from the HSV-2(G) BamHI F fragment with linkers containing 5' EcoRI and 3' Sal I restriction enzyme sites appropriate for cloning into the pGEX-5×-3 GST (Glutathione S transferase) fusion protein vector (Pharmacia, Piscataway, N.J.; see Studier, et al., Methods in Enzymology, 135:60) at the EcoRI and SalI sites in the polylinker of the vector. The ATG start codon of the 708 bp UL56 insert was changed to GTG. The amplified product was cloned in frame with the GST protein resulting in clone PAV116. FIG. 4 depicts the construction of PAV116, the GST-UL56 fusion protein expression vector. The GST-UL56 fusion protein was subsequently expressed by induction of a bacterial culture transformed with PAV116 using 1 mM IPTG (Sigma) for two hours. The induction of the predicted 52 kilodalton (kDa) fusion protein was checked by SDS polyacrylamide gel electrophoresis followed by staining with coomassie blue stain. This GST-UL56 fusion protein is characterized by having the GST polypeptide portion at the amino terminus of the fusion protein and the HSV-2 UL56 polypeptide portion at the carboxyl terminus of the fusion protein. This approximately 52 kDa fusion protein was purified by affinity chromatography with glutathione cross linked to agarose beads (Pharmacia). The purity of the preparation was checked by separation on denaturing polyacrylamide gels followed by staining with coomassie blue. The affinity purified preparation was used to immunize rabbits for the production of polyclonal antiserum. Another preparation of SDS polyacrylamide gel purifed GST-UL56 protein was used to further boost the rabbits following the initial immunization.

Production of Rabbit Polyclonal Antisera.

Antibodies to UL56 were generated according to the methods described in U.S. Pat. No. 5,922,328 (e.g., see Example 1 therein), which is incorporated by reference herein.

Polyacrylamide Gel Electrophoresis and Immunoblotting.

Vero cell monolayers were infected with the appropriate virus at a multiplicity of infection (MOI) of 5, and at 17 hours post infection the cells were harvested. The infected cell monolayers were washed, scraped into cold PBS and centrifuged to pellet the cells. The cell pellets were disrupted by addition of 350 ml of PBS A* (Phosphate buffered saline containing 1% NP40, 1% Sodium deoxycholate, 10 mM TPCK [Tosylsulfonyl phenylalanyl chloromethyl ketone], 10 mM TLCK [aTosylL-lysine chloromethyl ketone], 5 mM phenylmethylsulfonyl fluoride, 1 mg/ml pepstatin, and 17 mg/ml aprotinin). The proteins were electrophoretically separated in denaturing 10% polyacrylamide gels and the separated polypeptides were transferred to nitrocellulose according to the method of Towbin et al. (1979. Proc. Natl. Acad. Sci. USA 76: 4350-4354). Proteins were electroblotted in 50 mM Tris, 380 mM glycine, 20% methanol (pH 8.3) for 90 min 300 mA. Following transfer, the membrane was immersed in blocking buffer (5% skim milk in PBS) to block for 1 hour at room temperature or overnight at 4° C. The membrane was then washed briefly with a solution containing 1% BSA (bovine serum albumin) in PBS and incubated with the rabbit polyclonal antiserum for 1 hour at room temperature or overnight at 4° C. The membrane was washed in the blocking solution three times for 30 minutes and the bound rabbit antibodies were then detected by incubation of the membrane for 1 hour at room temperature with goat anti-rabbit IgG conjugated to alkaline phosphatase (Promega, Madison, Wis.). The membrane was then washed once with the blocking buffer and three more times with PBS and then developed with the substrates Nitro blue tetrazolium (NBT) and 5-bromo-4-chloro-3-indolyl (BCIP) (both from Promega, Madison Wis.). The reaction was stopped after 10 min by rinsing the membrane in a solution containing 100 mM tris pH 7.6 and 10 mM EDTA.

Example 2

Construction and Description of RAV 9395

Construction of Recombinant HSV-2 Viruses.

The intermediate recombinant HSV-2 viruses constructed prior to the recombinant HSV-2 virus, RAV 9395, and their genotypes and phenotypes are shown in Table 1. To exploit procedures for the construction of recombinant HSVs by insertion and deletion of a tk selectable marker as described elsewhere (Post and Roizman, Cell 25:227-232 (1981)), a HSV-2 (G) tk⁻ recombinant was first constructed. This recombinant, designated RAV 9364, was similar to HSV-1(F) Δ305 (Post et al., Cell 24:555-565 (1981)) in that it was tk⁻ and the plaques formed by RAV 9364 were syncytial, suggesting that the UL24 open reading frame on the strand opposite the tk gene (encoded by UL23) was also deleted. Jacobson et al., J. Virol. 63:1839 (1989). RAV 9364 served as the parent virus for all the recombinants constructed in this study.

Recombinant virus RAV 9364 is a genetically engineered deletion virus lacking a 498-bp BspEI fragment in the tk gene. RAV 9364 was constructed by co-transfection of rabbit skin cells with PAV14 (described below) along with intact plaque purified HSV-2 (G) DNA. Following transfection tk⁻ viruses were selected using BUdR. The 498 bp deletion of the tk coding sequence in RAV 9364 eliminates a BamHI restriction enzyme site and results in the fusion of HSV-2(G) BamHI N (approx. 4 kilobase pairs (kbp)) and BamHI ΔS (approx. 3.2 kbp). See Chartrand et al., *J. Gen. Virol.* 52:121-133 (1981) (FIG. 1 showing BamHI restriction map of HSV-2 strain HG52). This resulted in a fusion BamHI fragment of 7.2 kb, designated as BamHI ΔS+N.

Recombinant HSV-2 viruses were screened using Southern blots probed with PAV20. This screening detected an increase in size of BamHI S from 3.6 to 7.2 kbp. PAV20 is a plasmid containing BamHI S cloned into pGEM3zf+ (Promega, Madison, Wis.) as a probe.

To construct PAV14, the tk deletion plasmid, HSV-2(G) DNA was restriction enzyme digested with HindIII and the resulting subgenomic fragments were cloned into the HindIII restriction site of pGEM9zf–, a commercially available derivative of pGEM3zf+. The clones were screened with a fragment of the HSV-2(G) tk gene amplified using PCR primers selected on the basis of conserved sequences among herpesvirus tk genes, including HSV-1 and HSV-2 tk genes and in particular, due to its sequence availability, the tk gene of HSV-2 strain 333 (Kit et al., *Biochim. Biophys. Acta,* 741:158 (1983)), and labeled with $\alpha^{32}P$ by nick translation. The clone harboring the HSV-2(G) HindIII H DNA fragment (Chartrand et al. (J. Gen. Virol. (1981)) containing the HSV-2 (G) tk gene was designated PAV6. An EcoRI-HindIII fragment of approximately 3.6 kbp, harboring the tk sequence, was excised from PAV6 and cloned into pGEM9Zf– to generate PAV9. A 498 bp BspEI tk fragment was removed from PAV9 and the resulting clone was designated PAV14. One object of the present invention is to provide a live, attenuated HSV-2 virus that is incapable of replicating in and destroying the CNS tissue, wherein said HSV-2 virus lacks a functional ICP34.5 protein.

To engineer deletions or introduce modifications into the $\gamma_1 34.5$ gene RAV 9365, a recombinant virus was constructed which carried two copies of the HSV-1(F) tk gene driven by the HSV-1(F) α27 promoter (α27tk) inserted in both copies of the $\gamma_1 34.5$ gene within the HSV-2(G) genome. It was constructed by co-transfecting rabbit skin cells with intact RAV 9364 viral DNA and PAV16 which contains the 1.7 kbp α27tk chimeric gene inserted into the $\gamma_1 34.5$ gene contained in the BamHI V fragment within the HSV-2 genome. Following transfection tk$^+$ recombinant viruses were selected. The tk$^+$ recombinant viruses were screened for by the presence of the α27tk gene in BamHI V and BamHI G by Southern hybridization using both nick translated pRB3968 containing α27tk sequences to confirm insertion of the tk gene and with PAV2 (described below) to detect the increase in size of the BamHI V and G by 700 bp due to the insertion. To construct PAV16, a 1620 bp SphI fragment was excised from pRB801, a clone containing the BamHI UV junction fragments of HSV-2 (G) cloned into the BamHI site of pUC8, a commercially available plasmid. The 1620 bp SphI fragment was inserted into the SphI site of PAV1, a derivative of pGEM3Zf+ in which the EcoO109I restriction enzyme site was destroyed by cleavage with EcoO109I, blunt ending with T4 polymerase and religating to generate PAV2. The α27tk chimeric gene was excised from pRB3968 as an NcoI fragment and inserted into PAV2 cleaved with EcoO109I by rendering the vector and the fragment blunt ended with T4 polymerase. The 1.7 kbp α27tk gene replaces 1033 bp of HSV-2(G) sequence including 923 bp of the 939 bp ICP34.5 open reading frame and the resulting plasmid was designated PAV5. To restore flanking sequences for recombination of the chimeric gene into the viral genome, the 2.5 kbp SphI fragment containing the α27tk gene within the ICP34.5 open reading frame was excised from PAV5 by partial digestion and cloned into pRB801 cleaved with SphI. The resulting plasmid was designated PAV16.

Recombinant virus RAV 9366, containing a 923 bp deletion in both copies of the $\gamma_1 34.5$ gene was generated by co-transfecting intact RAV 9365 viral DNA with PAV15. In this PAV15 plasmid, nearly all of the coding sequence of the $\gamma_1 34.5$ gene had been deleted. The recombinant viruses were selected. The expected genomic structure was confirmed by hybridization of electrophoretically separated restriction enzyme digests of viral DNA with radiolabeled PAV2. To construct PAV15, PAV2 was digested with EcoO109I, blunt ended with T4 polymerase and religated to generate PAV3. A 587 bp SphI fragment was excised from PAV3 and cloned into pRB801 cleaved with SphI generating PAV15.

Recombinant virus RAV 9369, was constructed by co-transfection of PAV9 with intact RAV 9366 viral DNA and tk$^+$ viruses were selected, plaque purified and screened for the restoration of BamHI N and S indicating that the tk gene had been restored. To ensure that no additional mutations had occurred in the genome as a result of the manipulations of the virus, the ICP34.5 gene sequences were restored in RAV 9369 to generate recombinant virus RAV 9372.

To design a recombinant virus suitable for a live attenuated vaccine it is possible to over-attenuate the virus and consequently negate its utility as a vaccine. To minimize this possibility, a gradation of additional deletions were introduced into RAV9369. The choice of genes to delete or mutate was based on several observations. 1. R7020 a prototype of a live, attenuated, genetically engineered vaccine for HSV-1 contained deletions in UL55 and UL56. 2. The avirulent phenotype of HFEM, an HSV-1 based isolate could be abolished by allowing expression of the HSV-1 UL56 gene. Rosen-Wolff et al., Virus Research 20:205 (1991) 3. HSV-2(G) based viruses deleted in UL55 and UL56 showed decreased protein synthesis relative to wild type, indicating possible attenuation. Therefore, deletions in genes UL56 and UL55 were introduced into RAV 9366, generating RAV 9392 and 9394, respectively. The tk gene was repaired in each of RAV 9392 and RAV 9394, generating RAV 9393 and RAV 9395, respectively.

To construct RAV 9393 and RAV 9395, an α27tk chimeric gene from HSV-1(F) was inserted into the UL56 sequences of RAV 9366, the tk$^-$ parent virus of RAAV 9369, by co-transfection of RAV 9366 viral DNA with PAV27. tk$^+$ progeny viruses were selected and plaque purified. Viruses were screened for the insertion of the α27tk gene by a 1.2 kbp increase in HSV-2 (G) BamHI F fragment and the resulting tk$^+$ recombinant was designated RAV 9391. RAV 9392, containing a 446 bp deletion in the UL56 gene was constructed by co-transfection of intact RAV 9391 DNA and PAV26 onto rabbit skin cells and selection and plaque purification of tk$^-$ viruses. Viruses were screened by Southern analyses for a 446 bp decrease in the BamHI F fragment with PAV23 as a probe. RAV 9394 harbors a 1336 bp deletion in the Bam HI F fragment. The deletion removes the entire UL56 open reading frame and almost all of the UL55 gene except for 102 bp which still remain at the N-terminus of the UL55 open reading frame. RAV 9394 was constructed by co-transfection of RAV 9391 with PAV49. Finally the tk gene was restored by co-transfection of PAV9 with RAV 9392 or RAV 9394 DNA onto rabbit skin cells and selection of tk$^+$ viruses RAV 9393 and RAV 9395, respectively.

To construct PAV27, the HSV-2(G) 6848 bp BamHI F fragment was cloned into pGEM3zf+ generating PAV24. A chimeric 1.7 kbp α27tk gene from HSV-1(F) was cloned into PAV24 at the NcoI sites and the resulting clone designated PAV27. PAV24 was digested with NcoI and religated to generate PAV26. PAV49 was generated by digestion of PAV26 with NcoI and BsgI, the vector was rendered blunt ended with T4 polymerase and religated. The 1682 bp HSV-2(G) HindIII O fragment was cloned into pGEM9Zf.⁻ generating PAV23 which was used as the probe to screen for recombinant viruses deleted in UL56 and UL55.

Description of RAV 9395

The HSV-2 recombinant virus construct designated as RAV 9395 was specifically designed to eliminate the expression of three herpesvirus proteins, ICP34.5, and the proteins encoded by genes UL55 and UL56. To accomplish this RAV 9395 harbored a 1033 bp deletion encompassing 923 bp of the ICP34.5 gene. It stretched from the EcoO109I site located 16 bp from the start codon (ATG) of the ICP34.5 open reading frame to the EcoO109I site located 110 bp after the stop codon of the ICP34.5 open reading frame. As the ICP34.5 gene is present in two copies in the viral genome, the deletion described above was engineered into both copies of the ICP34.5 open reading frame. Additionally, RAV 9395 also contains a large deletion in the UL56 and the UL55 genes. All of the UL56 gene is deleted and only the first 102 bp of the UL55 gene remain (because the UL55 and UL56 genes are in opposite orientation). The deletion stretches from the NcoI site at the start codon of the UL56 gene and extends to the BsgI site located 102 bp from the start codon of the UL55 open reading frame. All site locations are based on the published sequence of HSV-2 strain HG52. McGeoch et al. (1991) Finally, the tk gene in recombinant virus RAV 9395 is intact and functional.

TABLE 1

Recombinant viruses generated en route to RAV 9395

| VIRUS | GENOTYPE | PHENOTYPE |
|---|---|---|
| HSV-2 (G) | wild type | tk+ |
| RAV 9364 | ΔUL23, ΔUL24 | tk− |
| RAV 9365 | ΔUL23, ΔUL24, γ₁34.5i | tk+, ICP34.5− |
| RAV 9366 | ΔUL23, ΔUL24, Δγ₁34.5 | tk+, ICP34.5− |
| RAV 9369 | Δγ₁34.5 | tk+, ICP34.5− |
| RAV 9372 | Δγ₁34.5R | tk+, ICP34.5+ |
| RAV 9375 | ΔUL23, ΔUL24, UL56i | tk+, UL56− |
| RAV 9376 | ΔUL23, ΔUL24, ΔUL56 | tk+, UL56− |
| RAV 9377 | ΔUL56 | tk+, UL56− |
| RAV 9378 | ΔUL23, ΔUL24; ΔUL55, ΔUL56 | tk−, UL55−, UL56− |
| RAV 9379 | ΔUL55, ΔUL56 | tk+, UL55−, UL56− |
| RAV 9380 | ΔUL23, ΔUL24, UL56α4H943epi | tk−, UL56α4tag |
| RAV 9381 | ΔUL56R | tk+, UL56+ |
| RAV 9391 | ΔUL23, ΔUL24, Δγ₁34.5, | tk+, UL56− |
| RAV 9392 | ΔUL23, ΔUL24, Δγ₁34.5, | tk−, ICP34.5−, UL56− |
| RAV 9393 | Δγ₁34.5, ΔUL56 | tk+, ICP34.5−, UL56− |
| RAV 9394 | Δγ₁34.5, ΔUL23, ΔUL24, ΔUL55, ΔUL56 | tk−, UL55−, UL56−, ICP34.5− |
| RAV 9395 | Δγ₁34.5, ΔUL55, ΔUL56 | tk+, UL55−, UL56−, ICP34. | i denotes an insertion mutant e.g., α27tk insertion;
R denotes a repair virus;
Δ denotes a deletion virus and
α4tag denotes a mutant with an HSV-1 α4 epitope tag.

Description of FIG. 1

FIG. 1 is a schematic representation of the DNA sequence arrangement in the genomes of HSV-2(G) and the recombinant viruses en route to the RAV 9395. The following section describes FIG. 1.

Line 1 represents the sequence arrangement of the HSV-2 genome. The filled rectangles represent the internal inverted repeats ab, b'a'c', and ca. The HSV-2(G) a sequence is present in a direct orientation at the two genomic termini and in the inverted orientation at the junction between the long and short components, $U_L$ and $U_S$, respectively. Flanking the internal inverted repeat sequences are the unique sequences (represented by thin lines) of the long and short components of the viral DNA. The hollow, outlined arrows represent the ICP0 and ICP34.5 open reading frames which are present in two copies in the viral genome, in the ab and in the b'a'c' inverted repeats. The solid blocked arrows indicate the UL56 and the UL55 open reading frames respectively. The thin black arrow indicates the position of the thymidine kinase (tk) gene.

At Line 2, the relevant Bam HI fragments are indicated as V, S, N, F, and U. The letter G indicates the BamHI G fragment which is a fusion of the BamHI fragments U and V in the illustrated prototype genome organization. The two letters H indicate the HindIII sites of the HindIII O fragment of HSV-2 (G) which is located within the HSV-2(G) BamHI F fragment. The letters B indicate the BspEI sites within the tk gene which flank the 498 bp fragment which is deleted in all the tk-viruses constructed in this study. The removal of the small BspEI fragment also deletes the BamHI site between the BamHI S and the BamHI N fragments.

Line 3 indicates the viral DNA used as probes for the identification of the recombinant viruses. PAV20 is an HSV-2 BamHI S fragment cloned into pGEM3f+. PAV23 is an HSV-2 HindIII O fragment cloned into pGEM9zf⁻. PAV2 contains a 1620 bp SphI fragment from the HSV-2 BamHI G fragment cloned into pGEM3zf+.

Line 4 shows an expansion of the region of viral DNA showing the positioning and orientation of the UL55, UL56 genes and the genes encoding the ICP0 and ICP34.5 gene products.

Line 5 illustrates the genome organization of RAV 9365. This recombinant virus harbors the 498 bp BspEI deletion in the tk gene and also carries a 1.7 kb α27tk gene inserted in place of the 1003 bp EcoO 109I fragment within the 1620 bp SphI fragment in the HSV-2(G) BamHI V and G fragments. E=EcoO109I. Sp=SphI.

Line 6 shows the genome organization of RAV 9366. This recombinant harbors the 498 bp BspEI deletion in the tk gene together with a 1003 bp deletion in the viral genome within HSV-2 BamHI fragments V and G. The resulting deletion virus therefore harbors a 923 bp deletion in both copies of the ICP34.5 gene. Recombinant virus RAV 9369 has the same deletion at the ICP34.5 locus but the BspEI 498 bp fragment has been restored in its genome and the tk gene is functional. E=EcoO109I.

Line 7 illustrates the genome organization of recombinant virus RAV 9391. This recombinant also harbors a 923 bp deletion in both copies of the ICP34.5 gene as indicated and carries a deletion of 498 bp in the tk gene as defined by the BspEI fragment. RAV 9391 carries an α27tk chimeric gene in place of a 446 bp NcoI fragment within the UL56 gene located in the HSV-2 BamHI F fragment. N=NcoI.

Line 8 depicts the genome organization of recombinant virus RAV 9395. This virus carries the 1003 bp deletion in the HSV-2 BamHI V and G fragments resulting in a 923 bp deletion in both copies of the ICP34.5 gene. RAV 9395 also carries a 1336 bp deletion within the HSV-2 BamHI F fragment encompassing both the UL56 and the UL55 genes. This deletion encompassing the UL56 and UL55 genes stretches from the NcoI site located at the ATG of the UL56 gene to the BsgI site located 102 bp from the start of the UL55 open reading frame. The 498 bp BspEI fragment is restored at the tk locus and the resulting RAV9395 is therefore tk+ and the tk gene is functional. Bs=BsgI.

Southern Analyses of Recombinant Viruses En Route to RAV 9395

Figure 2A:
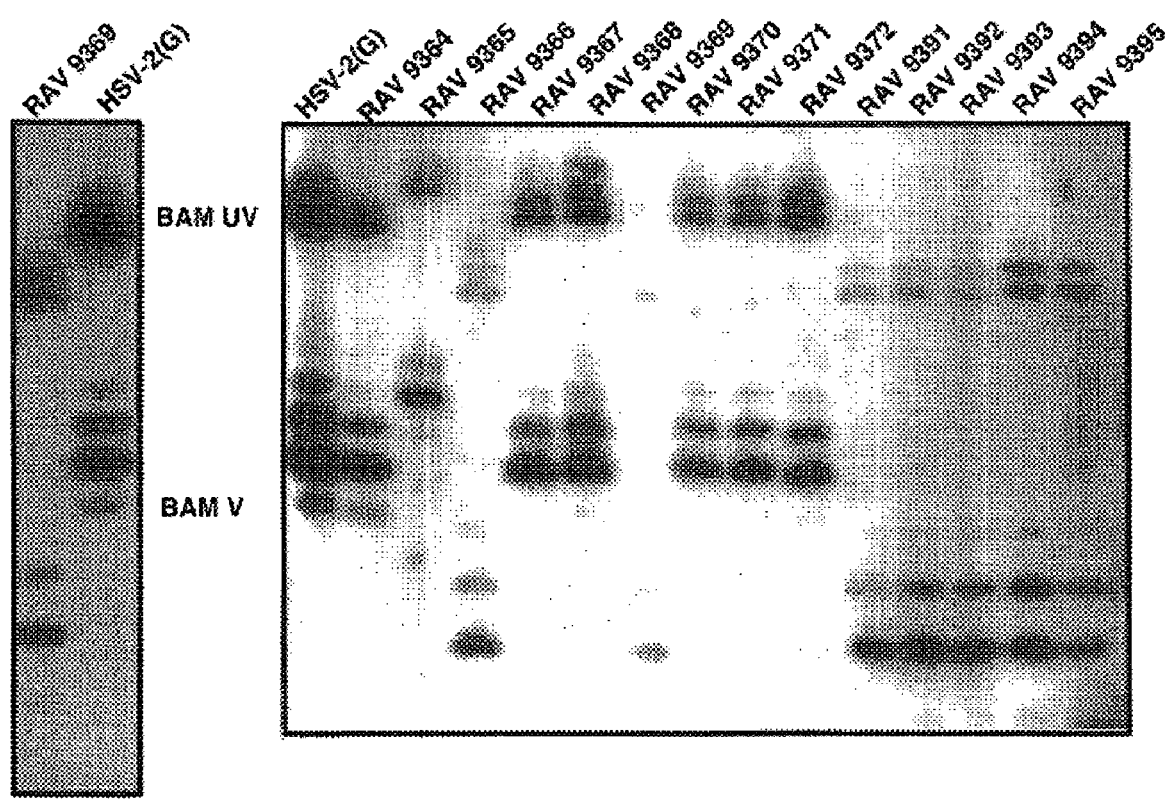
FIG. 2A is a Southern analysis of recombinant HSV-2 viruses en route to recombinant HSV-2 virus RAV 9395.

FIG. 2A illustrates autoradiographic images of BamHI digests of HSV-2 wild-type and recombinant mutant viral DNAs. Viral DNA digests were electrophoretically separated on 0.8% agarose gels, transferred to Hy-bond nylon membranes, and hybridized with specific radiolabeled probes. The viral DNA in both panels was probed with radiolabelled PAV2 which contains $\gamma_1 34.5$ specific sequences together with flanking sequences. BamHI V (Bam V) and BamHI UV (Bam UV) fragments are shown. The multiple banding pattern obtained is due to the heterogeneity of the viral a sequences which are labelled with this probe.

Figure 2B:
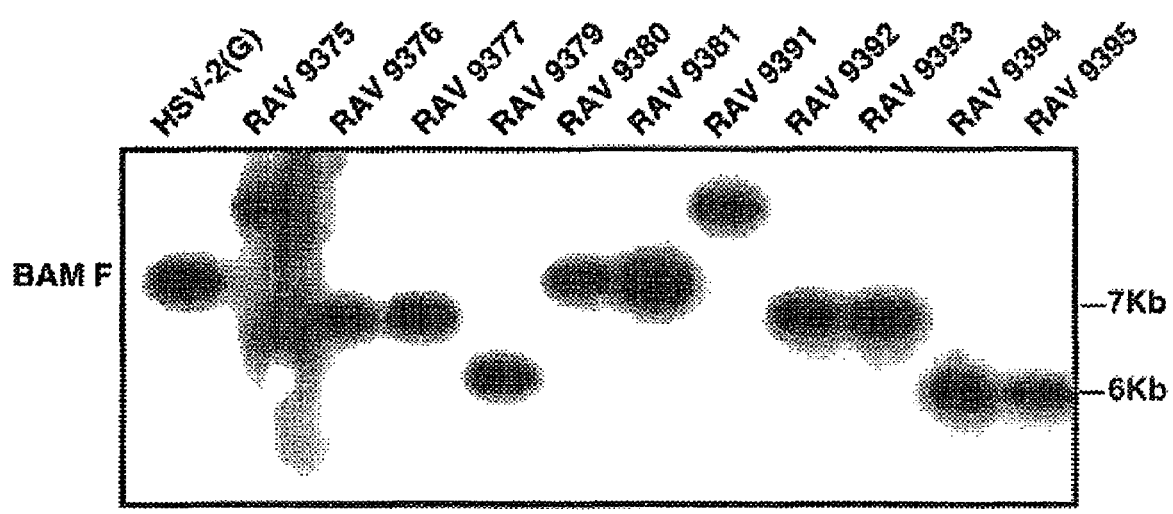
FIG. 2B is a Southern analysis of HSV-2 recombinant viruses with deletions in the UL55 and UL56 genes, probed with the HSV-2(G) BamHI F fragment.

FIG. 2B illustrates autoradiographic images of wild type and recombinant viral DNA digested with BamHI and electrophoretically separated on 0.8% agarose gels, transferred to Hybond nylon membranes and hybridized with radiolabeled PAV23. PAV23 contains the HindIII O fragment of HSV-2 (G) DNA and hybridizes to the BamHI F fragment which contains the UL55 and UL56 genes. The BamHI F fragment is indicated on the blot.

Figure 2C:
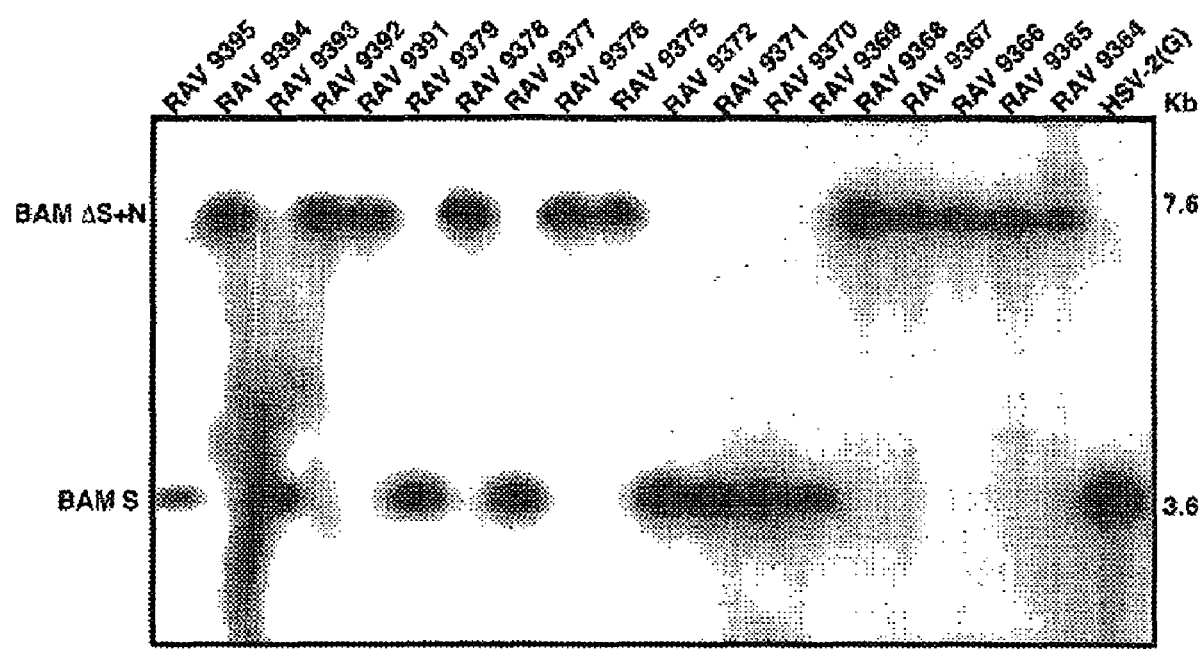
FIG. 2C is a Southern analysis of tk$^+$ and tk$^-$ recombinant viruses en route to development of recombinant HSV-2 virus RAV 9395.
Figure 3A:
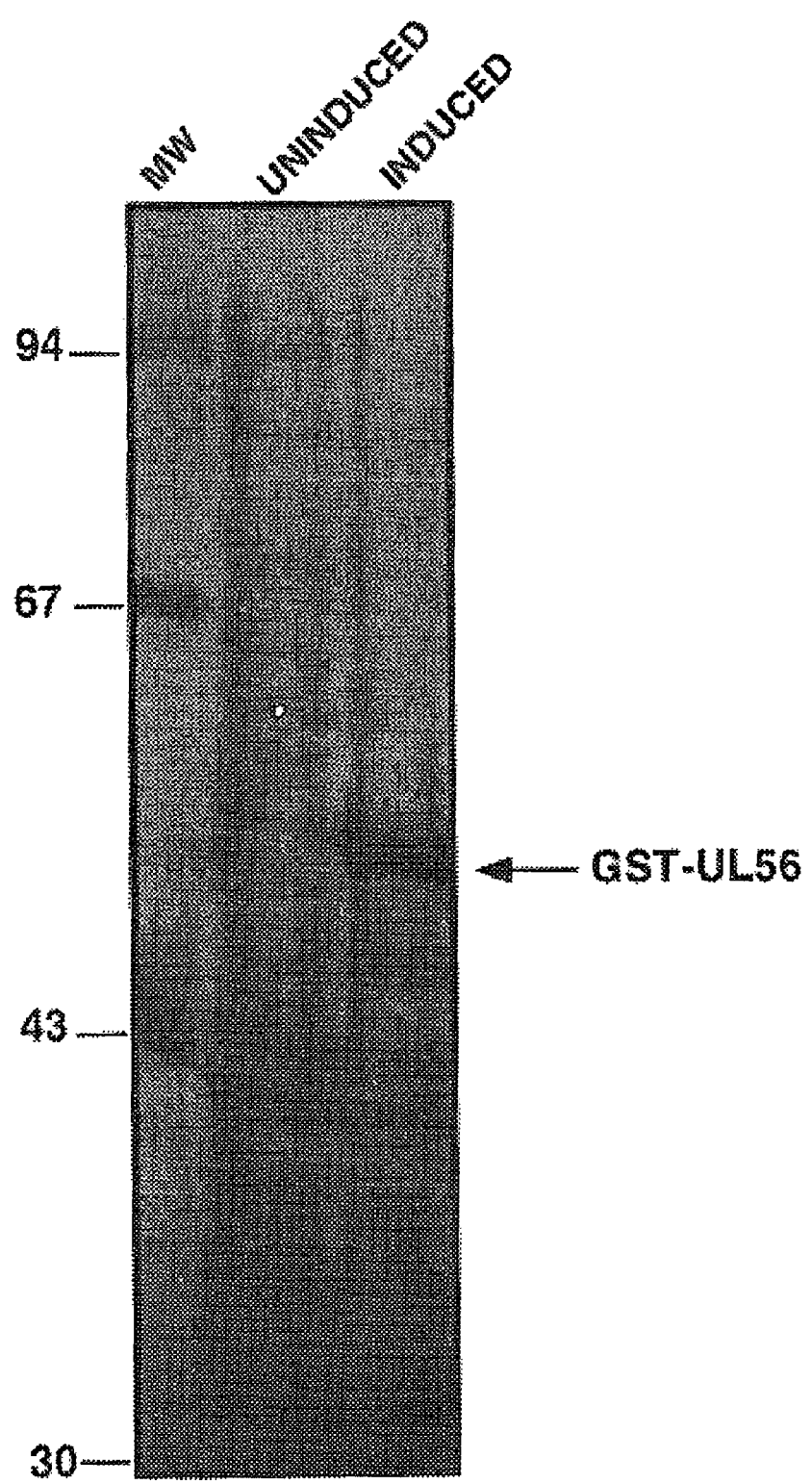
FIG. 3A is a Coomassie stained protein gel confirming induction by IPTG of a 52 kD GST-HSV-2 UL56 fusion protein in *E. coli*.
Figure 3B:
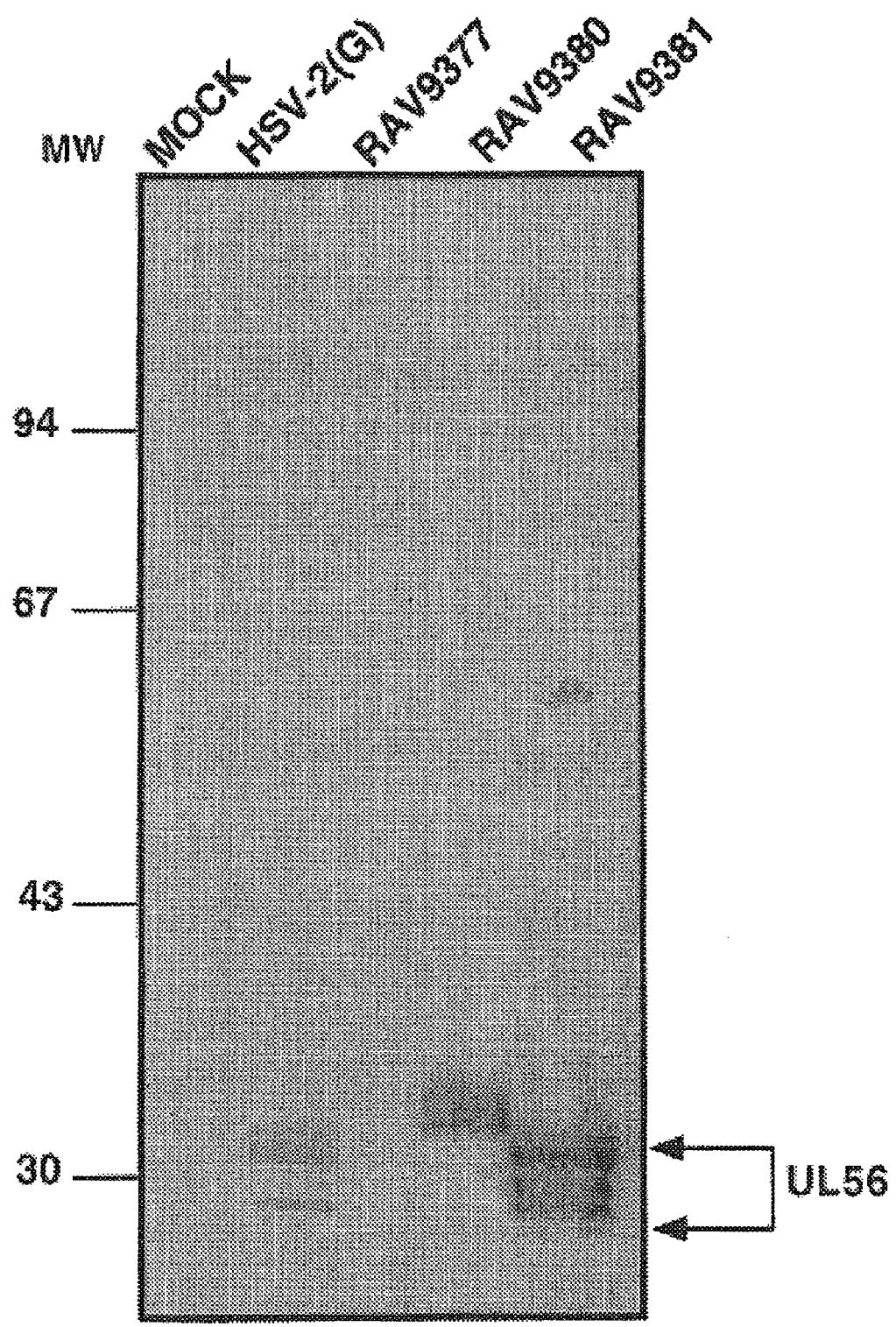
FIG. 3B is a Western blot showing the use of the polyclonal antiserum raised against the GST-UL56 fusion protein to demonstrate the expression or lack of expression of UL56 in the recombinant viruses leading up to RAV 9395.
Figure 3C:
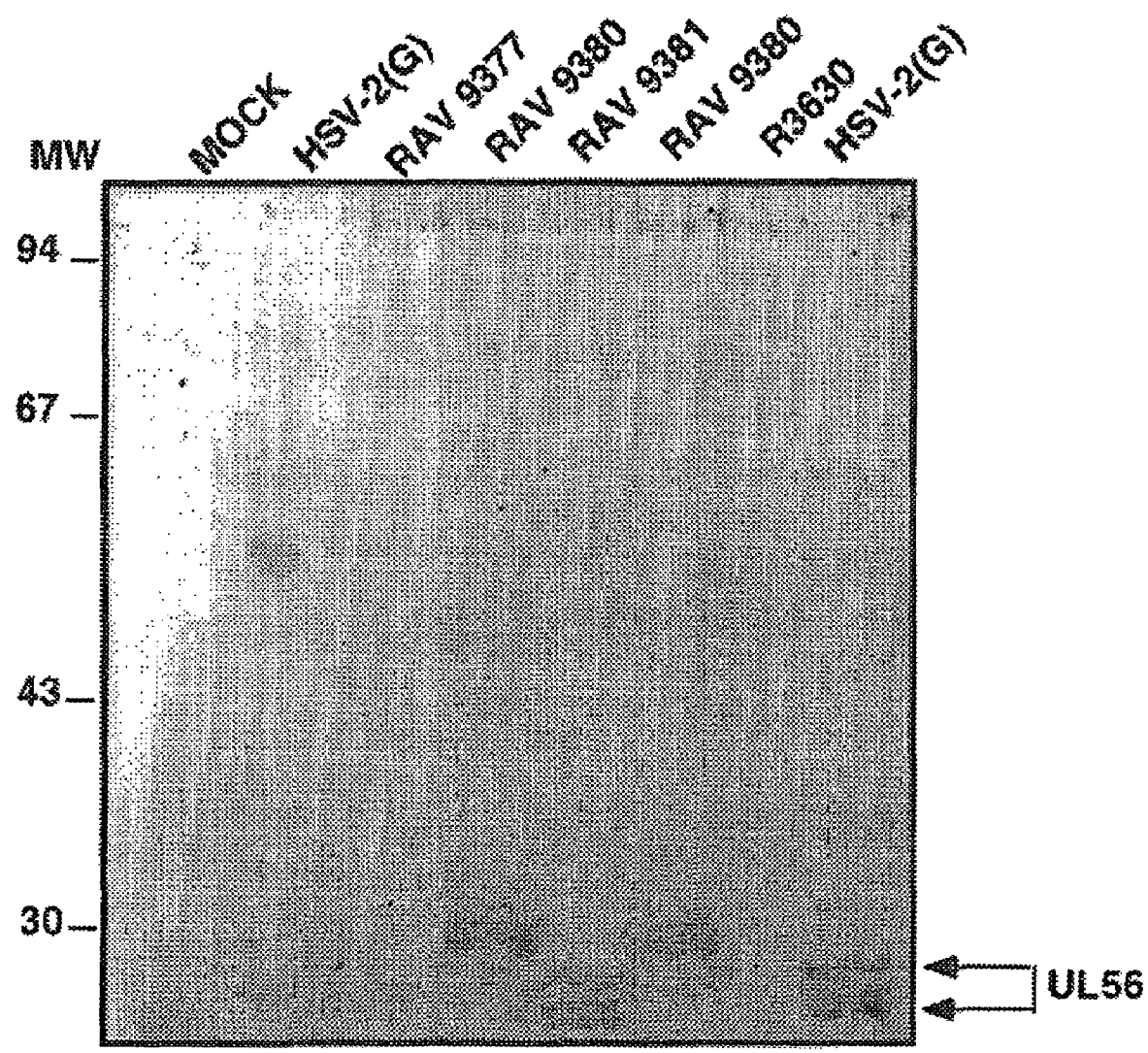
FIG. 3C shows a Western blot demonstrating that the polyclonal antiserum raised against the GST-UL56 fusion protein is specific for HSV-2 UL56 and does not specifically bind HSV-1 UL56 polypeptides.
Figure 3D:
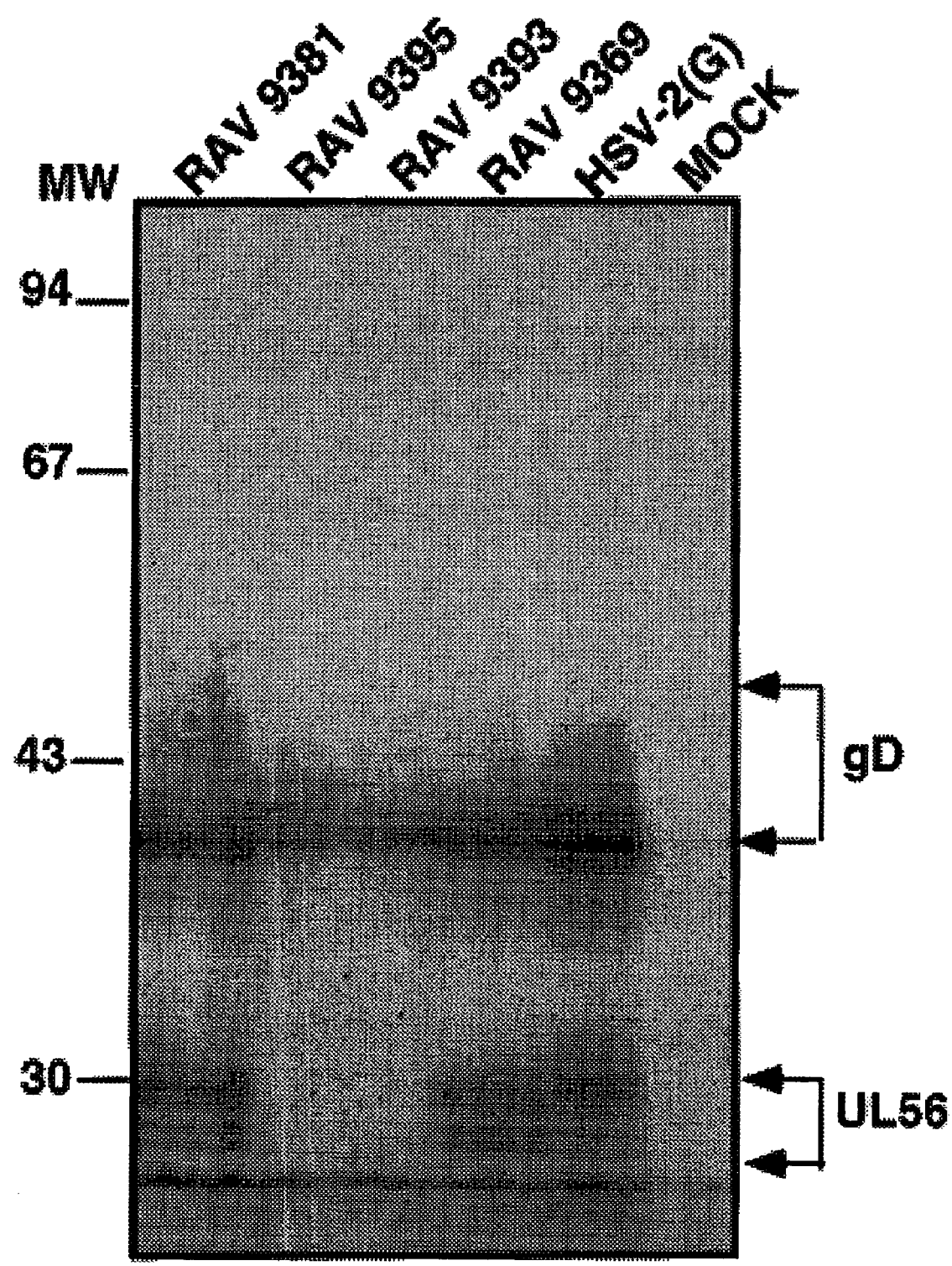
FIG. 3D shows that RAV 9395 does not express the UL56 gene product, via an immunoblot of RAV 9395 infected cell lysates and probing with the polyclonal antiserum raised against the GST-UL56 fusion protein.

FIG. 2C illustrates autoradiographic images of BamHI digests of wild type and recombinant viral DNAs electrophoretically separated on 0.8% agarose gels, transferred to Hybond nylon membranes and probed with radiolabelled PAV20, a clone containing sequences from the HSV-2 tk gene and its flanking sequences. BamHI S and the new band at approximately 7.2 kb due to the fusion of BamHI N with the deleted form of BamHI S are indicated.

Example 3

Preparation of RAV 9395 In Vero and MRC 5 Cell Lines

High titer stocks of RAV 9395 were prepared by two distinct methods. The choice of method was dependent on the cell line and the choice of cell line was contingent on whether the stock of virus was a research stock or for use as a potential vaccine in humans.

Preparation of High Titer RAV 9395 In Vero Cells.

Six roller bottle cultures of Vero cells were grown to 80% confluency at 37° C. The cultures were then infected with RAV 9395 at an input multiplicity of infectivity (MOI) of 0.001-0.01. The virus was allowed to adsorb for 1 hour at 37 degrees C. and the inoculum was replaced with fresh low serum media (see below). The infected cultures were incubated at 34° C. for 4 days until approximately 100% cytopathic effect (CPE) was observable.

The virally infected cells were then removed from the surface of the plastic bottles by vigorous shaking and the infected cells were sedimented by centrifugation at 2000 rpm for 10 minutes in sterile centrifuge bottles. The resulting supernatant was discarded and the pellet of infected cells was resuspended in 12 mls of a 50:50 mixture of low serum media (minimum essential medium (MEM) (JRH Biosciences, Lenexa, Kans.) supplemented with 1% fetal calf serum (FCS)) (JRH Biosciences, Lenexa, Kans.), L-glutamine (2 mM), penicillin (100 units/ml), streptomycin (0.1 mg/ml) and pyruvate (1 mM)), and sterile skim milk (90 g powdered milk, (Carnation) in 1 liter of sterile water and this solution was subjected to 3 rounds of autoclaving and cooling before it was added to the low serum media). The virus and cell suspension was then sonicated four to six times for 15 second intervals on ice with 2-5 min periods of cooling on ice between each sonication using a vertical probe sonicator. The virus solution was then aliquoted and shock frozen at −80° C. in an upright Harris freezer. An aliquot of the virus was titered on Vero cells after one freeze thaw cycle. The titers were routinely $1\times10^9$-$1\times10^{10}$ pfu per ml.

Preparation of RAV 9395 in MRC 5 Cells.

Six roller bottle cultures of growing MRC-5 cells were infected with RAV 9395 at a MOI of 0.08. After adsorption of the virus for 1 hour the inoculum was removed and replaced with fresh media. The infected cells were incubated for 4 days at 34-35° C. on a roller bottle apparatus turning at 0.5 rpm, until the cell layer showed maximum CPE. The culture media was discarded and the infected cell monolayers were washed with Dulbecco's phosphate buffered saline (DPBS). The cells were harvested and dounce homogenized using a tight pestle to thoroughly disrupt the cells. The virus/cell suspension was then stabilized by addition of 10×SPG (2.18M sucrose, 0.038M $KH_2$ $PO_4$, 0.072M $K_2$ $HPO_4$ and 0.054M L-glutamate).

Example 4

Generation of a GST-UL56 Fusion Protein and Antibody.

The outline for the methods for generation of the fusion protein and the polyclonal antibody is located in the Materials and Methods section above.

FIG. 3A is a photographic image of a coomassie blue stained 10% denaturing polyacrylamide gel showing electrophoretically separated proteins from cells transformed with PAV116, a plasmid containing the UL56 gene of HSV-2 cloned in frame with the Glutathione S transferase protein (GST-UL56). Lane 1 indicates the molecular weight standard proteins; lane 2 indicates 100 ug of protein extracted from uninduced cultures of bacteria transformed with plasmid PAV116; lane 3 indicates 100 ug of protein extracted from PAV116 transformed bacteria induced with 1 mM IPTG. The arrow indicates the induced GST-UL56 fusion protein migrating with the expected molecular weight of 52 kDa.

FIG. 3B is a photographic image of a Western blot of lysates of cells infected with the indicated recombinant viruses electrophoretically separated in denaturing gels, transferred to nitrocellulose and reacted with polyclonal anti-UL56 serum. The arrows indicate the UL56 specific signals. RAV 9381 is a repair of RAV 9377 which carries a deletion in the UL56 gene. RAV 9380 is a recombinant virus in which the UL56 open reading frame is tagged with a 17 amino acid epitope from the HSV-1 (F) $\alpha 4$ protein.

This polyclonal antibody is specific for HSV-2 UL56 and this is illustrated in FIG. 3C where there is no reaction from lysates with cells infected with the type 1 based recombinant R3630. As the UL56 gene is deleted in recombinant virus RAV 9395 lysates derived from cells infected with RAV 9395 do not express the UL56 gene product and this is illustrated in FIG. 3D which shows a photograph of an immunoblot of cells infected with RAV9395.

The blot shown in FIG. 3D was also probed with a specific monoclonal antibody to the HSV-2 glycoprotein D (gD) as a control for equal protein loading and infectivity.

Example 5

Safety and Efficacy of RAV 9395 in *Aotus trivirgatus* sp.

Three female *Aotus trivirgatus* sp. were immunized intramuscularly with RAV 9395 at doses of $10^3$, $10^4$ and $10^5$ plaque forming units (pfu), respectively. Thirty days post immunization, the *Aotus* were challenged intravaginally with a lethal dose of $10^2$ pfu of wild type HSV-2 (G). Although some weight loss was observed, the animals appeared to tolerate the challenge well. In contrast, two female *Aotus* inoculated intramuscularly with wild type HSV-2 (G) at $10^1$ and $10^2$ pfu, respectively, and without prior immunization with RAV 9395, had to be euthanized at day 14 and day 11.

In addition, one female *Aotus* was immunized intramuscularly with RAV 9395 at a dose of $10^6$ pfu. The animal exhibited some discharge at the injection site, some weight loss and some isolated lesions at distant sites probably resulting from autoinoculation. The lesions resolved and the animal is otherwise normal. The results of these experiments are summarized in Table 2, below.

The results of the *Aotus* experiment demonstrate a 5 log margin of safety between RAV 9395 and wild type HSV-2 (G). In addition, these experiments demonstrate the protective efficacy of RAV 9395 as a vaccine candidate in an animal model that is exquisitely sensitive to infection by HSV.

TABLE 2

Immunization of *Aotus* sp. with RAV 9395 results in protection from challenge with wt HSV-2 (G)

| Animal # | Virus | Result of Immunization | Challenge | Result of Challenge | Date of Euthanization |
|---|---|---|---|---|---|
| 418 | RAV 9395 | No lesions—slight weight loss | I Vag $10^2$ | Slight weight loss normal | |
| 509 | RAV 9395 | No lesions—slight erythema at injection site Weight loss | I Vag $10^2$ | Slight weight loss normal | |
| 438 | RAV 9395 | slight weight loss | I Vag $10^2$ | Slight weight loss normal | |
| 445 | RAV 9395 | Discharge from injection site—some weight loss otherwise normal | Not done | | |
| 411 | HSV-2(G) | Severe lesions viremia moribund | | | Day 14 |
| 331 | HSV-2(G) | Severe lesions viremia moribund | | | Day 11 |

IM = intramuscular inoculation;
I Vag = intravaginal inoculation

Example 6

Comparison of RAV 9395 and R7020 in *Aotus trivirgatus* sp.

Meignier et al. *J. Inf. Dis.* 162: 313 (1990) reported an extensive study of the behavior of a recombinant HSV type 1 vaccine candidate R7020, in *Aotus trivirgatus* sp. R7020 consists of the HSV-1 strain F genome with a defined number of internal deletions and insertions. Specifically, R7020 lacks (I) UL55, UL56, (ii) all of the internal inverted repeats of the prototype arrangement in the L component and the portion from the L/S junction to the EcoR1 site in the domain of the internal inverted repeat portion of the S component, (iii) 500 bp SacI-BglII fragment from the BamHI Q fragment. Included among the sequences deleted are a portion of UL23, a portion of UL24 and one copy each of α0, $\gamma_1$34.5, ORF P, ORF O, and one complete copy of the sequences which give rise to the Latency Associated Transcript (LAT). In place of the deleted sequences were inserted (a) a copy of the thymidine kinase gene fused in the correct orientation under the transcriptional control of the α4 gene promoter located in the remaining portion of the inverted repeats, and (b) a DNA fragment encoding the HSV-2(G) glycoprotein G. Their report documents the lack of significant side effects when R7020 was given *Aotus* at doses of $10^7$ pfu by intramuscular or subcutaneous routes. In addition, inoculation with $10^6$ pfu either intravaginally or via the ocular mucosa caused no harm to the animals.

The R7020 HSV recombinant was tested in a Phase 1 trial in humans (Abstract #341, 1992 ICAAC meeting). In seronegative recipients, the vaccine candidate was well tolerated. In HSV-1(+) seropositive individuals, reactogenicity was observed at the dose of $10^{4.5}$ TCID$_{50}$. Antibody increases were not observed in volunteers who were previously HSV-1(+) seropositive. A weak IgG response to HSV-1, but not to HSV-2, was detected by ELISA in seronegative subjects. Following two doses of R7020 at $10^{5.2}$ TCID$_{50}$, a strong ELISA IgG response was observed to HSV-1 and HSV-2. Neutralizing antibodies to HSV-1 were also observed in some volunteers. The R7020 vaccine candidate was not developed further possibly from a perspective that the candidate was over attenuated.

We have confirmed some of the in vivo characteristics in the *Aotus* monkey study reported by Meignier et al. When we administered R7020 at $10^6$ pfu intravaginally to one of the monkeys from the same cohort as discussed in Example 4, we observed that the virus was well tolerated at this dose and the monkey exhibited no signs of disease. As also discussed in Example 4, when RAV 9395 was given intramuscularly at $10^6$ pfu however, the animal exhibited some discharge at the injection site, some weight loss and some isolated lesions at distant sites probably resulting from auto-inoculation. The lesions resolved and the animal is otherwise normal. This different response indicates that RAV 9395 is less attenuated than R7020 in the *Aotus* monkey.

All publications and patent applications mentioned in this specification are herein incorporated by reference to the same extent as if each individual publication or patent application was specifically and individually indicated to be incorporated by reference.

Example 7

Construction of AD472

AD472 was constructed from a set of six overlapping cosmid clones that were cotransfected in Vero cells to produce infectious virus. Cosmids 9394.54 and 9394.67 cloned from RAV 9394 DNA, the tk⁻ predecessor of RAV 9395, and were used to recapitulate the same ICP34.5 and UL55-56 deletions as described in RAV 9395 [Spector et al., 1998]. Cosmid clone scpt43.5 was engineered to delete UL43.5 via a 7.3 kb deletion and cosmid AD467 was altered to delete the US10-12 region. These four cosmids were used to introduce the specific deletions in ICP34.5, UL55-56, UL43.5, and US10-12 and the remaining viral sequences required to produce infectious virus were supplied by cosmids GK5 and GK22. These six cosmids were cotransfected in triplicate flasks of Vero cells and the recombination of these cosmids resulted in the generation of infectious virus stocks in these cells. Three independent virus stocks were produced from the triplicate flasks and were designated, AD468, AD471 and AD472. Viral DNA was purified from each of these stocks and retransformed into MRC-5 cells to produce the master virus stocks used in this study. Although AD472 was constructed by the method described above, other techniques and methods that are well known in the art can also be utilized to construct AD472. See, e.g., Kemble et al., *J Virol* 1996 March;70(3):2044-8, which is incorporated by reference herein.

Example 8

Genetic Stability of AD472

The genetic stability of three independently derived isolates of the vaccine virus was assessed by the serial passage in the central nervous system of mice. For each isolate, a group of 10, 4 wk old male Balb/c mice were intracranially inoculated with approximately $1 \times 10^5$ PFU of the vaccine virus. At 72 hours post infection (hpi), the animals were sacrificed and the brains were extracted and homogenized. The very low levels of virus present in pooled brain homogenates was amplified in Vero cells to obtain enough virus to infect a second group of mice representing the second serial passage for each of these viruses. This process was repeated such that a total of 9 serial passages were performed, and the $LD_{50}$ of the virus stocks were determined at passage 1, 6, and 9 in 4 week old male Balb/c mice.

Passaged isolates of AD468, AD471, and AD472 were evaluated following passages 1, 6, and 9 to determine the $LD_{50}$ values at each of these passages (FIG. 6). Each of the independent isolates represented by the shaded and empy squares and the empty circles remained highly attenuated in the CNS even after 9 serial passages in this system suggesting that this specific set of mutations conferred both attenuation as well as genetic and phenotypic stability of the vaccine virus. They proved to be more stable than RAV9395 represented by the shaded circles.

Example 9

Replication and Attenuation in the Guinea Pig Model

Three groups of 15 guinea pigs were inoculated intravaginally with 3 concentrations of HSV-2 isolate AD472 for evaluation of pathogenicity. Two groups of 15 guinea pigs were inoculated intravaginally with 2 concentrations of wt HSV-2, strain G for comparison (HSV-2(G)). Animals were examined daily, lesions scored for severity and vaginal samples taken for quantitation of HSV replication. Dorsal lumbosacral ganglia samples were collected from 2 infected animals per group on Day 5 post-inoculation and 3 infected animals per group on Day 10 post-inoculation to determine the presence of infectious virus in the ganglia by co-cultivation on primary rabbit kidney fibroblasts. All surviving guinea pigs were anesthetized for collection of blood via cardiac puncture for determination of neutralizing antibodies on Day 28 post-inoculation. The remaining animals were observed for recurrent lesions through Day 56. Guinea pigs were then anesthetized for a final blood collection and euthanasia.

Figure 7:
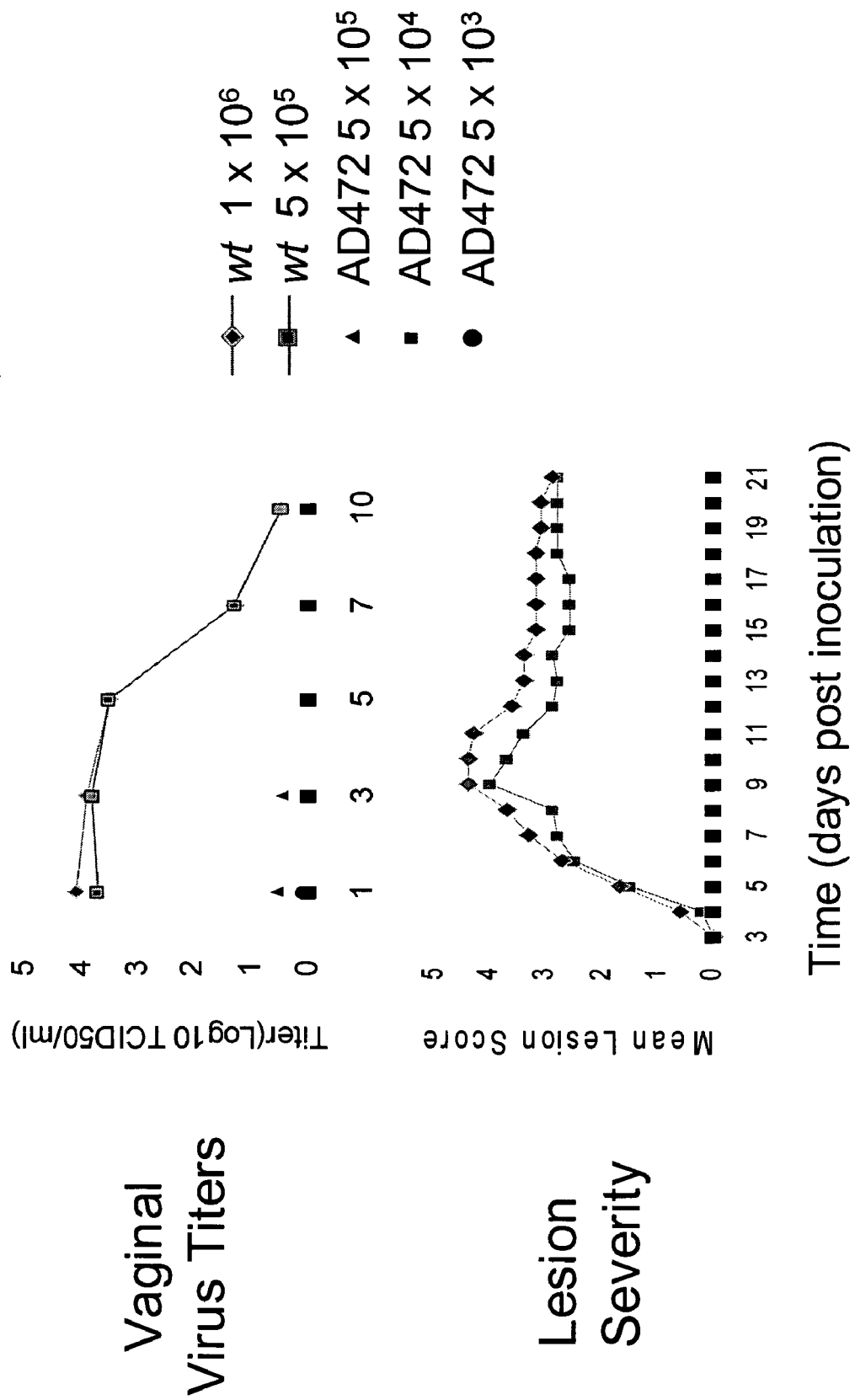
FIG. 7 is a diagram depicting the attenuation of AD472 in a guinea pig.

The guinea pig model was used to confirm the attenuated nature of the vaccine candidate and to establish the replication characteristics in this model. Groups of 10 animals were infected intravaginally with AD472 and lesion score as well as virus shedding were monitored in these animals for 21 days following infection. Animals inoculated with $5 \times 10^5$ PFU of AD472 did not develop vaginal lesions and shed low levels of virus, predominantly during the first few days following inoculation (FIG. 7). By contrast, infection with HSV-2(G) produced severe pathology in this model and high titers of virus were shed at least a week following infection. The large differences in lesion development and replication between animals inoculated with AD472 or HSV-2(G) demonstrated that the vaccine virus is highly attenuated in this model and does not appear to be reactogenic. Essentially no lesions were observed in animals inoculated with AD472 throughout the study. The low infection rates, lack of viral replication and absence of lesions indicate that the mutant virus AD472 is highly attenuated. In contrast, animals inoculated with HSV-2(G) all developed lesions and had a typical course of infection. Guinea pigs inoculated with HSV-2(G) developed lesions, most of which resolved by Day 21, and experienced recurrence rates (# of animals with recurrence/# possible) of 3/3 and 2/3, with an average length of time for recurrence incidence lasting 2.6 or 3.8 days for the HSV-2(G) at $1 \times 10^6$ or $5 \times 10^5$ pfu/ml, respectively. Of the two guinea pigs that had recurrences and were infected with HSV-2(G) at $1 \times 10^6$ pfu/ml, one animal had a single recurrence and the other had 2. Of the three guinea pigs that had recurrences and were infected with HSV-2(G) at $5 \times 10^5$ pfu/ml, two animals had a single recurrence and the other had 3. Animals inoculated with AD472 had no evidence of virus at either Day 5 or Day 10 post inoculation, whereas HSV-2(G) was present in all of samples from Day 5.

Serum 50% neutralization titers from guinea pigs infected intravaginally with AD472 or HSV-2(G) were obtained. Animals inoculated with $5 \times 10^5$ AD472 developed titers ranging from about 200 at the high dose to <10 at the low dose, while animals infected with the wt virus were typically in the range of 1000-3000.

Example 10

Protection from Challenge with the Wild Type Virus

Figure 8:
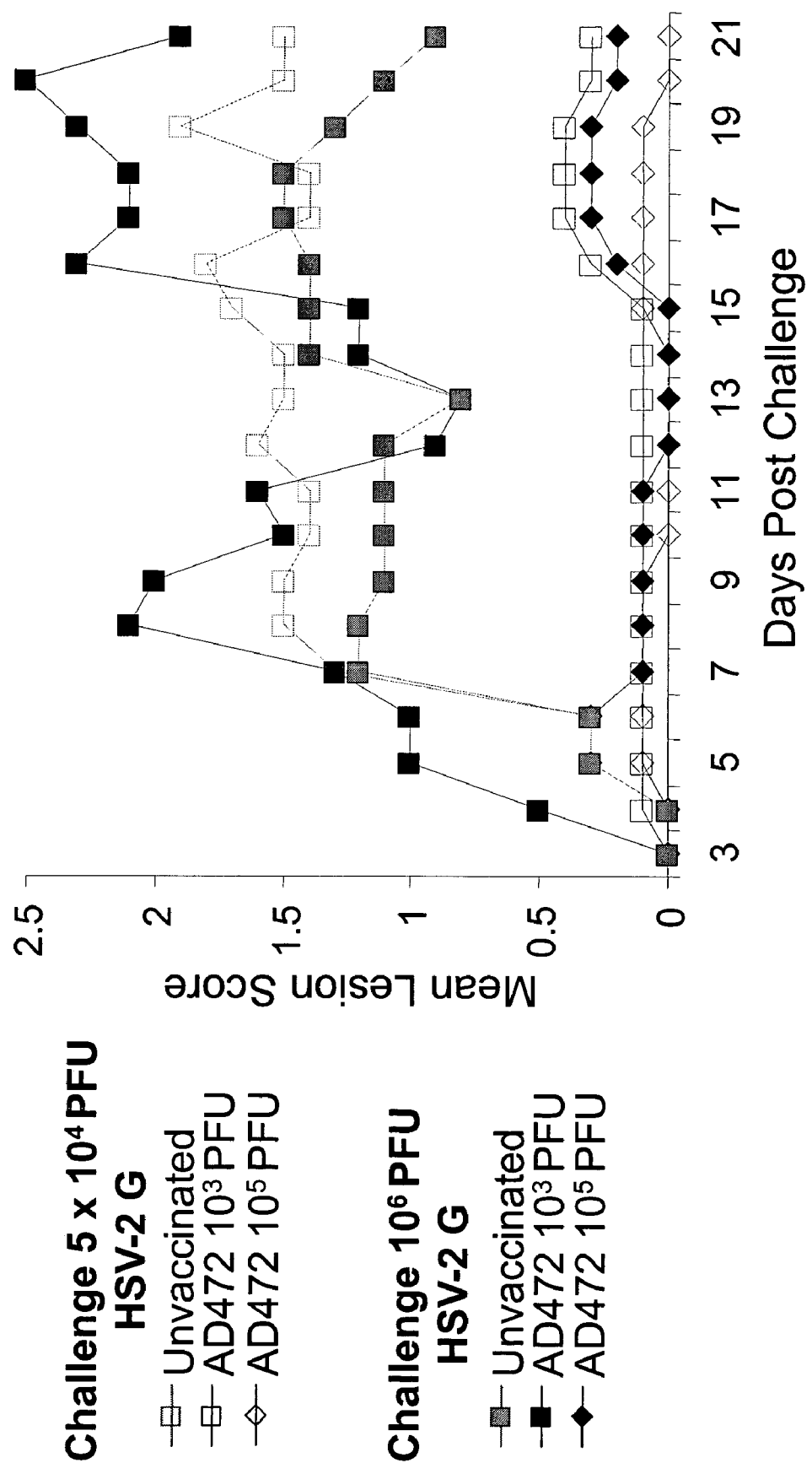
FIG. 8 is a diagram depicting challenge studies of wild-type HSV-2 infection after a vaccination with AD472.

The development and severity of the genital lesions are summarized in FIG. 8. Immunization with AD472 at $1 \times 10^5$ pfu did significantly reduce the lesion-day AUC (p<0.001) from 18.3 to 2.5 when the higher infection challenge of HSV-2(G) was used at $1 \times 10^6$ pfu/ml. Additionally, the mean peak lesion scores were reduced significantly (p<0.05) from 1.9 to 0.4. AD472 at $1 \times 10^3$ pfu was not effective. When guinea pigs were immunized with AD472 at $1 \times 10^5$ or $1 \times 10^3$ pfu and challenged with HSV-2(G) at $5 \times 10^4$ pfU/ml, significant reductions in the lesion-day AUC (p<0.001) occurred, as well as, in mean peak lesion scores (p<0.01). Recurrence rates (# of animals with recurrence/# possible) were low in all groups. The control groups, which received HSV-2(G) without immunization had rates of 11.1% and 0% for the $5 \times 10^4$ or $1 \times 10^6$ pfu/ml infections respectively. Animals immunized with 3 or 5 logs of AD472 and challenged with $1 \times 10^6$ PFU of wt virus had recurrence rates of 18% and 15%, respectively. Guinea pigs vaccinated with 3 or 5 logs of AD472 and challenged with $5 \times 10^4$ PFU of wt virus exhibited recurrence rates of 7.1% and 6.6%, respectively.

When HSV-2(G) at $1 \times 10^6$ pfu/ml was used as the challenge dose, there were no differences seen between immunized and non-immunized animals regarding viral replication in lesions. However, when HSV-2(G) at $5 \times 10^4$ pfu/ml was used as the challenge dose, both immunized groups had reduced titer-day AUC values of 5.8 versus the non-immunized group value of 12.0. The AD472 group given $1 \times 10^3$ pfu i.m. was significantly lower (p<0.05) compared to the control. Non-immunized groups infected with HSV-2(G) had 60-80% of recovered ganglia positive for HSV-2. Immunization with $1 \times 10^3$ pfu of AD472 did not reduce viral recovery from ganglia of vaccinated animals following the HSV-2(G) challenge at $1 \times 10^6$ pfu/ml, but virus could be isolated only from 20% ganglia from animals challenged with $5 \times 10^4$ pfU/ml of wt virus. AD472 immunization with $1 \times 10^5$ pfu reduced viral recovery in ganglia to 20% (NS) or 0% (p<0.05) with challenge doses of $1\times10^6$ or $5\times10^4$, respectively, compared to the non-immunized controls. See Table 3 for a summary.

TABLE 3

| Vaccination Group (AD472) | Challenge Dose (HSV-2(G)) | Positive Ganglia/ Number Cultures (Percent Positive) |
|---|---|---|
| Unvaccinated | $5 \times 10^4$ | 4/5 (80%) |
| $1 \times 10^3$ | $5 \times 10^4$ | 1/5 (20%) |
| $1 \times 10^5$ | $5 \times 10^4$ | 0/5 (0%) |
| Unvaccinated | $1 \times 10^6$ | 3/5 (60%) |
| $1 \times 10^3$ | $1 \times 10^6$ | 3/5 (60%) |
| $1 \times 10^5$ | $1 \times 10^6$ | 1/5 (20%) |

Prior to virus challenge, the guinea pigs vaccinated with $1\times10^5$ AD472 had a combined mean 50% neutralizing antibody titer of $138.5\pm63.9$ compared to animals immunized with AD472 at $1\times10^3$ pfu which had a combined mean neutralizing antibody titer of $11.2\pm21.8$. After challenge with the wt virus, the antibody neutralization titers for all vaccinated animals were boosted above 1000. Guinea pigs immunized with HSV-2, strain AD472 using $1\times10^5$ pfu and challenged with HSV-2(G) using $1\times10^6$ pfu/ml had a mean titer of 1176.5 which was significantly higher (p<0.05) than the 357.2 of the non-immunized group challenged intravaginally with HSV-2(G) using $1\times10^6$ pfu/ml.

The results discussed above demonstrate that AD472 is genetically and phenotypically stable and, when used as a vaccine in guinea pigs, AD472 does not produce lesions and was well tolerated. This vaccine was also effective in protecting animals from subsequent challenge with the wt virus as determined by decreased lesion score. Despite the large reduction in lesion score, the vaccine did not appear to reduce vaginal virus titers.

The invention now being fully described, it will be apparent to one of ordinary skill in the art that many changes and modifications can be made thereto without departing from the spirit or scope of the appended claims.

The specification and sequence listing of U.S. Pat. No. 5,922,328 is incorporated by reference herein.

What is claimed is:

1. An attenuated HSV-2 virus stock, wherein the HSV-2 virus stock is AD472.

* * * * *

UNITED STATES PATENT AND TRADEMARK OFFICE
CERTIFICATE OF CORRECTION

| | |
|---|---|
| PATENT NO. | : 7,592,169 B2 |
| APPLICATION NO. | : 10/830609 |
| DATED | : September 22, 2009 |
| INVENTOR(S) | : Spaete et al. |

It is certified that error appears in the above-identified patent and that said Letters Patent is hereby corrected as shown below:

On the cover page, item [*] Notice: Subject to any disclaimer, the term of this patent is extended or adjusted under 35 USC 154(b) by 218 days Delete the phrase "by 218 days" and insert -- by 501 days --

Signed and Sealed this

Eighth Day of June, 2010

David J. Kappos
*Director of the United States Patent and Trademark Office*